US008399689B2

(12) United States Patent
Bewley et al.

(10) Patent No.: US 8,399,689 B2
(45) Date of Patent: Mar. 19, 2013

(54) CHRYSOPHAENTIN ANTIMICROBIAL COMPOUNDS THAT INHIBIT FTSZ PROTEIN

(75) Inventors: Carole A. Bewley, Bethesda, MD (US); Alberto Plaza, Arlington, VA (US); Jessica Keffer, Rockville, MD (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 0 days.

(21) Appl. No.: 13/578,803

(22) PCT Filed: Feb. 25, 2011

(86) PCT No.: PCT/US2011/026220
§ 371 (c)(1),
(2), (4) Date: Aug. 13, 2012

(87) PCT Pub. No.: WO2011/106630
PCT Pub. Date: Sep. 1, 2011

(65) Prior Publication Data
US 2012/0316227 A1 Dec. 13, 2012

Related U.S. Application Data

(60) Provisional application No. 61/308,911, filed on Feb. 27, 2010.

(51) Int. Cl.
*C07D 323/00* (2006.01)
*C07C 43/275* (2006.01)
*C07C 43/295* (2006.01)
(52) U.S. Cl. ...................... 549/348; 568/635
(58) Field of Classification Search .................. 549/348; 568/635
See application file for complete search history.

(56) References Cited

U.S. PATENT DOCUMENTS

| 5,948,889 | A | 9/1999 | de Boer et al. |
| 7,718,651 | B2 | 5/2010 | White et al. |
| 2009/0221568 | A1 | 9/2009 | Shaw et al. |

OTHER PUBLICATIONS

Andreu, et al., "The Antibacterial Cell Division Inhibitor PC190723 is an FtsZ Polymer-Stabilizing Agent that Induces Filament Assembly and Condensation," *J. Biol. Chem.*, 285(19):14239-46, 2010 (Abstract only).
Czaplewski, et al., "Antibacterial Alkoxybenzamide Inhibitors of the Essential Bacterial Cell Division Protein FtsZ," *Bioorganic & Medicinal Chemistry Letters*, 19(2):524-527, 2009 (Abstract only).
Dasgupta, "Novel Compound with Potential of an Antibacterial Drug Targets FtsZ Protein," *Biochem. J.*, 423(e1-e3), 2009.
Domadia, et al., "Berberine Targets Assembly of *Escherichia coli* Cell Division Protein FtsZ," *Biochemistry*, 47:3225-3234, 2008.
Domadia, et al., "Inhibition of Bacterial Cell Division Protein FtsZ by Cinnamaldehyde," *Biochemical Pharmacology*, 74:831-840, 2007.
Giger, et al., "Libraries for Receptor-Assisted Combinatorial Synthesis (RACS). The Olefin Metathesis Reaction," *Synlett*, 6:688-691, 1998.
Green, et al., "Colpol, a New Cytotoxic $C_6$-$C_4$-$C_6$ Metabolite from the Alga *Colpomenia sinuosa*," *Journal of Natural Products*, 56(7):1201-1202, 1993.
Haydon, et al., "An Inhibitor of FtsZ with Potent and Selective Anti-Staphylococcal Activity," *Science*, 321(5896):1673-1675, 2008 (Abstract only).
International Search Report and Written Opinion, dated Oct. 20, 2011, issued in corresponding International Application No. PCT/US2011/026220.
Jaiswal, et al., Totarol Inhibits Bacterial Cytokinesis by Perturbing the Assembly Dynamics of FtsZ, *Biochemistry*, 46(14):4211-4220, 2007 (Abstract only).
Jennings, et al., "Design and Synthesis of Indolo[2,3-a] Quinolizin-7-One Inhibitors of the ZipA-FtsZ Interaction," *Bioorganic & Medicinal Chemistry Letters*, 14(6):1427-1431, 2004 (Abstract only).
Jennings, et al., Combinatorial Synthesis of Substituted 3-(2-Indolyl) piperidines and 2-phenyl indoles as Inhibitors of ZipA-FtsZ Interaction, *Bioorganic & Medicinal Chemistry*, 12(19):5115-5131, 2004 (Abstract only).
Kapoor, et al., "Targeting FtsZ for Antibacterial Therapy: A Promising Avenue," *Informa Healthcare*, 13(9). (doi:10. 1517/14728220903173257) (Abstract only), 2009.
Lock et al., "Cell-Division Inhibitors: New Insights for Future Antibiotics," *Nature Reviews Drug Discovery*, doi:10.1038/nrd2510, 7:324-338, 2008 (Table 3 and Abstract only).
Margalit, et al., "Targeting Cell Division: Small-Molecule Inhibitors of FtsZ GTPase Perturb Cytokinetic Ring Assembly and Induce Bacterial Lethality," *PNAS*, 101(32):11821-11826, 2004.
Mukherjee, et al., "N-Benzyl-3-Sulfonamidopyrrolidines as Novel Inhibitors of Cell Division in *E. coli*," *Bioorg. Med Chem Lett.*, 17(23):6651-5, 2007 (Abstract only).
PC190723-Compound Summary (CID 25016417), deposited by ChemIDplus, *PubChem*, 4 pages, 2008.
Plaza, et al., "Chrysophaentins A-H, Antibacterial Bisdiarylbutene Macrocycles that Inhibit the Bacterial Cell Division Protein FtsZ," *J Am Chem. Soc.*, 132:9069-9077, 2010.
Rai, et al., "Curcumin Inhibits FtsZ Assembly: An Attractive Mechanism for its Antibacterial Activity," *Biochem. J.*, 410(1):147-55, 2008 (Abstract only).
Reynolds, et al., "A New 2-Carbamoyl Pteridine that Inhibits Mycobacterial FtsZ," *Bioorganic & Medicinal Chemistry Letters*, 14(12):3161-3164, 2004 (Abstract only).
Runge, et al., "New Selectivities from Old Catalysts. Occlusion of Grubbs' Catalysts in PDMS to Change their Reactions," *J. Organomet. Chem.*, 691:5278-5288, 2006.
Sutherland, et al., "Structure-based Design of Carboxybiphenylindole Inhibitors of the ZipA-FtsZ Interaction," *Org. Biomol. Chem.*, http://pubs.rsc.org/doi:10.1039/B312016C, 1:4138-4140, 2003.

(Continued)

*Primary Examiner* — Kristin Bianchi
(74) *Attorney, Agent, or Firm* — Woodcock Washburn LLP

(57) ABSTRACT

Embodiments of antimicrobial chrysophaentin compounds, pharmaceutical compositions including the chrysophaentin compounds, and methods for using the chrysophaentin compounds are disclosed. Some embodiments of the disclosed compounds are isolated from *Chrysophaeum taylori*. Certain embodiments of the chrysophaentin compounds inhibit FtsZ protein, thereby inhibiting the growth of clinically relevant bacteria, including drug-resistant strains.

36 Claims, 8 Drawing Sheets

OTHER PUBLICATIONS

Urgaonkar, et al., "Synthesis of Antimicrobial Natural Products Targeting FtsZ: (±)-Dichamanetin and (±)-2'''-Hydroxy-5''-benzylisouvarinol-B," *Organic Letters*, 7(25):5609-5612, 2005.

Wang, et al., "Discovery of a Small Molecule that Inhibits Cell Division by Blocking FtsZ, a Novel Therapeutic Target of Antibiotics," *The Journal of Biological Chemistry*, 278(45):44424-44428, 2003.

White, et al., "2-Alkoxycarbonylaminopyridines: Inhibitors of *Mycobaterium tuberculosis* FtsZ," *Journal of Antimicrobial Chemotherapy*, 50:111-114, 2002.

Yu, et al., "Inhibition of Assembly of Bacterial Cell Division Protein FtsZ by the Hydrophobic Dye 5,5'-Bis-(8-anilino-1-naphthalenesulfonate)," *The Journal of Biological Chemistry*, 273(17):10216-10222, 1998.

H-3 100%
H-14 100%
H-12 98%
H-3' 98%
H-8 50%
H-6' 50%
H-6 40%

H-8' overlapped
H-12', H-14' not observed

CHRYSOPHAENTIN ANTIMICROBIAL COMPOUNDS THAT INHIBIT FTSZ PROTEIN

CROSS REFERENCE TO RELATED APPLICATIONS

This application is the U.S. National Stage of International Application No. PCT/US2011/026220, filed Feb. 25, 2011, published in English under PCT Article 21(2), which claims the benefit of U.S. Provisional Application No. 61/308,911, filed Feb. 27, 2010, which is incorporated by reference herein in its entirety.

FIELD

This disclosure relates generally to antimicrobial compounds and methods for their use.

BACKGROUND

There is an ongoing need to identify new lead compounds with novel mechanisms of action to treat infections caused by multi-drug resistant bacteria. Infectious diseases are the leading cause of death worldwide, and it has been estimated that in the United States more people die from methicillin-resistant *Staphylococcus aureus* (MRSA) related infections than from HIV. Moreover, the prevalence of invasive infections is reported to have risen with the increasing numbers of patients infected with HIV, receiving cancer therapy or treatment with broad-spectrum antibiotics. In fact 90,000 people die from hospital-acquired bacterial infections in the United States each year in part due to the fact that clinically important bacteria have developed multiple antibiotic resistance to drugs of last resort such as fluoroquinolones, vancomycin, and carbapemens. One reason for the development of antimicrobial resistance is the ability of infectious organisms to adapt quickly to new environmental conditions. The innate adaptability of microbes is complemented by the widespread and sometimes inappropriate use of antimicrobial drugs.

The dearth of new antimicrobials over the past several decades together with the increases in reported incidences of drug-resistant bacterial infections underscores the urgency of the need for new antibiotics. Disclosed herein are embodiments of novel compounds, which inhibit the growth of several bacterial strains, including drug-resistant strains.

SUMMARY

A new class of chrysophaentin antibiotics has been discovered. In specific embodiments, eight novel broad-spectrum antibiotics, chrysophaentins 1-8, belonging to a new structural class were isolated from the yellow alga *Chrysophaeum taylori*. Their structures were determined by extensive 2D NMR and MS techniques and are characterized by the presence of two polyhalogenated, polyoxygenated ω,ω'-diarylbutene units connected by two ether bonds to form a macrocyclic natural product. Chrysophaentin 1, the most potent of these antibiotics, inhibited the growth of clinically relevant Gram-positive bacteria including methicillin-resistant *Staphylococcus aureus* ($MIC_{50}$ 1.8±0.6 μg/mL) and vancomycin-resistant *Enterococcus faecium* ($MIC_{50}$ 2.8±0.8 μg/mL). Moreover, in vitro enzyme assays and transmission electron microscopy showed chrysophaentin 1 to inhibit the GTPase activity of the bacterial cytoskeletal protein FtsZ with an $IC_{50}$ value of 6.7±1.7 μg/mL, as well as GTP-induced formation of FtsZ protofilaments. Saturation Transfer Difference (STD) NMR experiments further confirmed chrysophaentin 1 binding to FtsZ, and NMR competition experiments with GTP-γ-S showed chrysophaentin 1 and GTP to bind competitively to FtsZ. Molecular docking showed chrysophaentin 1 to bind in and occlude a large portion of the GTP binding site of FtsZ using a surface that is consistent with the binding epitope determined by STD NMR.

As used herein, the terms "chrysophaentin" and "chrysophaentin compound" refer to polyhalogenated, polyoxygenated molecules that have the general formula I, II, or III, and pharmaceutical salts thereof. Formulas I, II, and III are shown below:

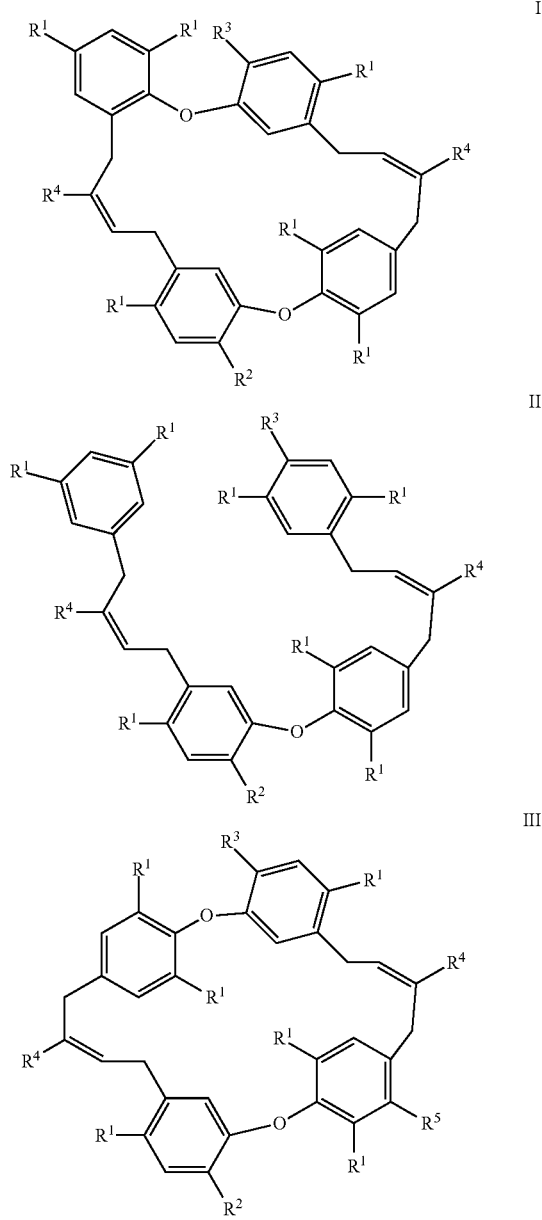

where each $R^1$ is independently hydrogen, hydroxyl, thiol, halogen, lower alkyl, lower alkoxy, or lower alkyl ester; and $R^2$, $R^3$, $R^4$, and $R^5$ independently are hydrogen, hydroxyl, thiol, or halogen. In some embodiments, each $R^1$ is independently hydroxyl or lower alkyl ester; $R^2$, $R^3$ and $R^4$ are each independently halogen; and $R^5$ is hydrogen or halogen. In particular embodiments, $R^1$ is hydroxyl, $R^2$ and $R^3$ independently are chloro or bromo, $R^4$ is chloro, and $R^5$ is hydrogen or bromo. In some embodiments, the chrysophaentin compounds have the same structures as antibiotic agents of these general structures found in *C. taylori*.

Certain embodiments of disclosed chrysophaentin compounds are represented by formulas IV, V, and VI, with the substituent combinations shown below:

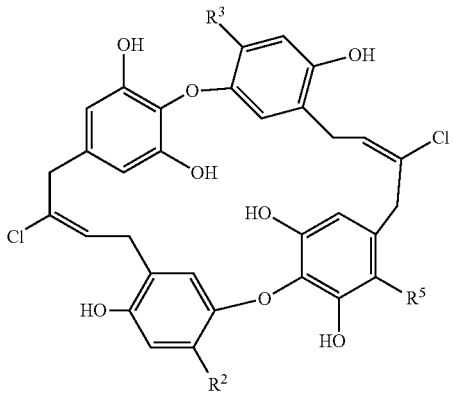

VI

6 $R^2$ = Cl $R^3$ = Cl $R^5$ = H
7 $R^2$ = Cl $R^3$ = Br $R^5$ = H
8 $R^2$ = Cl $R^3$ = Cl $R^5$ = Br

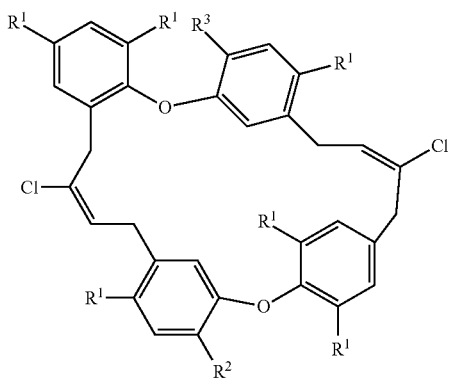

IV

1 $R^1$ = OH $R^2$ = Cl $R^3$ = Cl
1a $R^1$ = Ac $R^2$ = Cl $R^3$ = Cl
2 $R^1$ = OH $R^2$ = Br $R^3$ = Cl
3 $R^1$ = OH $R^2$ = Cl $R^3$ = Br
4 $R^1$ = OH $R^2$ = Br $R^3$ = Br

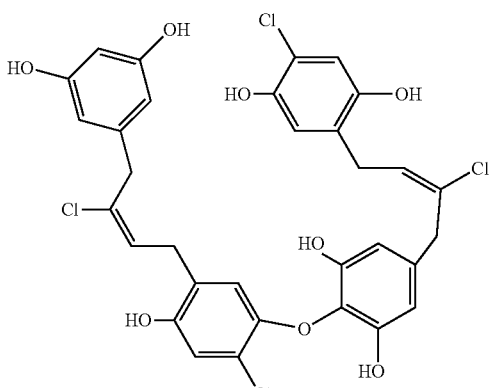

V

5

Specific examples of chrysophaentins 1-8 are shown above.

At least some embodiments of the disclosed compounds or derivatives thereof have a $MIC_{50}$ in the range of 1 to 25 µg/mL when applied to at least one bacterial strain. Certain embodiments are effective at inhibiting the growth of *Staphylococcus aureus*, *Enterococcus faecium*, *Bacillus subtilis*, methicillin-resistant *Staphylococcus aureus* (MRSA), multidrug-resistant *Staphylococcus aureus* (MDRSA), and/or vancomycin-resistant *Enterococcus faecium*. Embodiments of the disclosed compounds include pharmaceutical compositions comprising a pharmaceutically acceptable carrier and a therapeutically effective amount of at least one compound or mixture of compounds according to formula I, II, or III are disclosed herein.

Also disclosed are embodiments of a method for inhibiting bacterial cell growth, comprising exposing a bacterium to an effective amount of a composition comprising a chrysophaentin, for example, a chrysophaentin compound isolated from a marine organism, a derivative of a chrysophaentin compound or a combination thereof. In other embodiments, the compound or derivative thereof is a chrysophaentin having a structure according to formula I, II, or III. In other embodiments, the method further includes exposing the bacteria to an effective amount of a second agent other than the chrysophaentin, for example by including the second agent in a composition with the chrysophaentin. The second agent may be an antimicrobial agent, such as an antimicrobial agent effective against Gram-negative bacterial cells. In certain embodiments, the second agent increases penetration of the chrysophaentin into the bacterium, thereby increasing the composition's effectiveness. In some embodiments, the bacterium is exposed to the composition by administering a therapeutically effective amount of the composition to a subject in need of antimicrobial treatment. In certain embodiments, the chrysophaentin inhibits bacterial cell growth by inhibiting bacterial cell division protein FtsZ.

The foregoing and other objects, features, and advantages of the invention will become more apparent from the following detailed description, which proceeds with reference to the accompanying figures.

DETAILED DESCRIPTION

I. Abbreviations and Explanations of Terms

Figure 1:
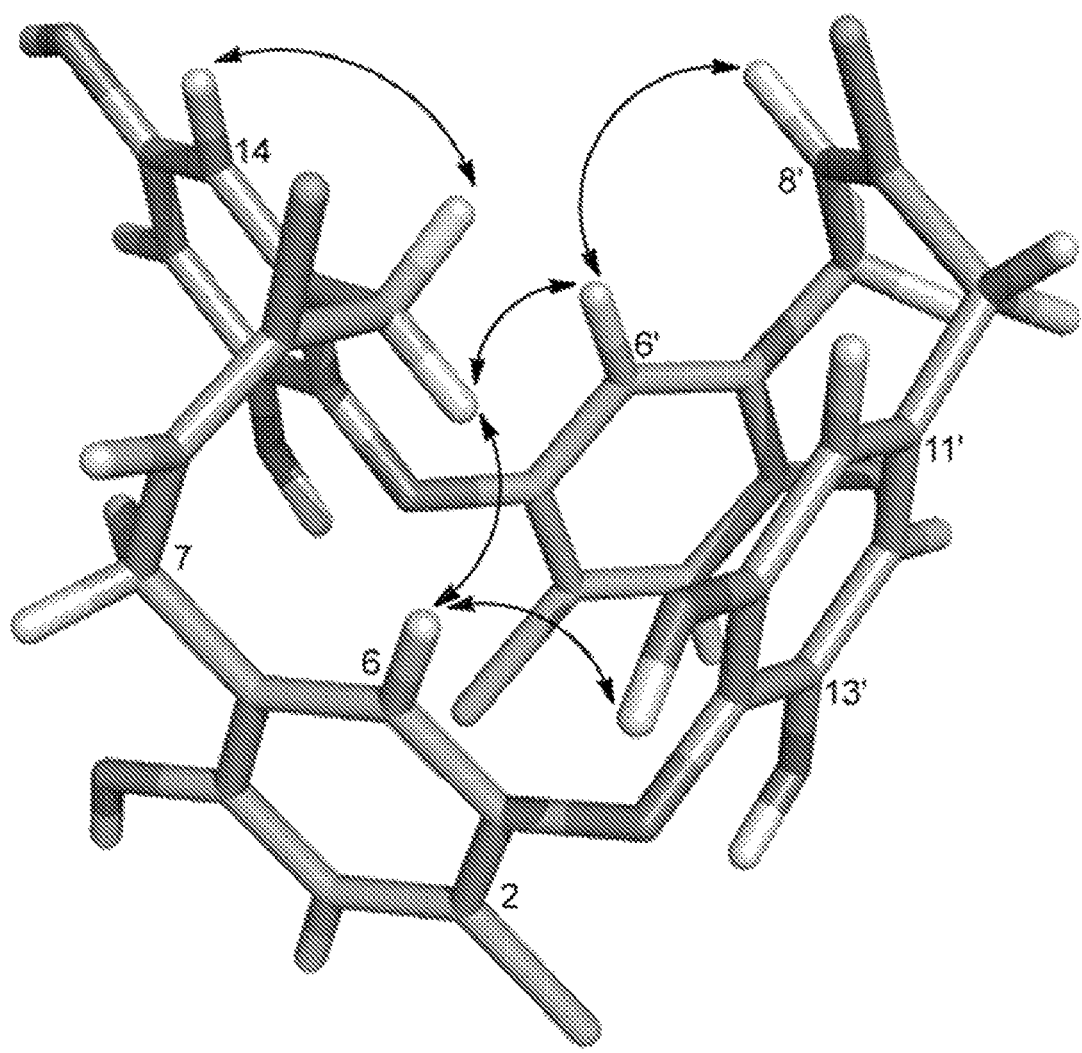
FIG. 1 is a 3D model of chrysophaentin 1.

The following explanations of terms and abbreviations are provided to better describe the present disclosure and to guide those of ordinary skill in the art in the practice of the present disclosure. As used herein, "comprising" means "including" and the singular forms "a" or "an" or "the" include plural references unless the context clearly dictates otherwise. The term "or" refers to a single element of stated alternative elements or a combination of two or more elements, unless the context clearly indicates otherwise.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting. Other features of the disclosure are apparent from the following detailed description and the claims.

Unless otherwise indicated, all numbers expressing quantities of components, molecular weights, percentages, temperatures, times, and so forth, as used in the specification or claims are to be understood as being modified by the term "about." Accordingly, unless otherwise indicated, implicitly or explicitly, the numerical parameters set forth are approximations that may depend on the desired properties sought and/or limits of detection under standard test conditions/methods. When directly and explicitly distinguishing embodiments from discussed prior art, the embodiment numbers are not approximates unless the word "about" is recited.

ABBREVIATIONS

AMBER: assisted model building with energy refinement
amu: atomic mass units
COSY: correlation spectroscopy
GTP: guanosine-5'-triphosphate
GTPase: an enzyme capable of binding and hydrolyzing GTP
HMBC: heteronuclear multiple-bond connectivity
HR-ESI-MS: high resolution electrospray ionization mass spectrometry
HSQC: heteronuclear single quantum coherence
$IC_{50}$: concentration resulting in a 50% inhibition of a biological or biochemical function
IR: infrared
LC-MS: liquid chromatography-coupled mass spectroscopy
MeOH: methanol
$MIC_{50}$: minimum concentration required to inhibit the growth of 50% of organisms
NMR: nuclear magnetic resonance
ROE: rotating-frame Overhauser enhancement
ROESY: rotating-frame NOE (nuclear Overhauser effect) spectroscopy
STD NMR: saturation transfer difference nuclear magnetic resonance
TEM: transmission electron microscopy
TFA: trifluoroacetic acid
TIC: total ion chromatogram

EXPLANATIONS OF TERMS

The following explanations of terms are provided to better delineate the subject matter of the present disclosure and to guide those of ordinary skill in the art in its practice.

All chemical compounds include either or both of the (+) and (−) stereoisomers, as well as any geometric isomers, such as Z and E isomers and cis and trans isomers. Other chemistry terms herein are used according to conventional usage in the art, as exemplified by *Hawley's Condensed Chemical Dictionary*, Richard J. Lewis, Sr. (ed.), published by John Wiley & Sons, Inc., 1997 (ISBN 0-471-29205-2).

Aliphatic: A substantially hydrocarbon-based compound, or a radical thereof (e.g., $C_6H_{13}$, for a hexane radical), including alkanes, alkenes, alkynes, including cyclic versions thereof, and further including straight- and branched-chain arrangements, and all stereo and position isomers as well. Aliphatic groups can be unsubstituted or substituted with one or more substituents, e.g., halogen, alkyl, alkoxy, hydroxyl, carboxyl, aryloxy, aryl, arylalkyl, heteroaryl, amino, alkylamino, dialkylamino, or other functionality.

Alkyl: A hydrocarbon group having a saturated carbon chain. The chain may be cyclic, branched or unbranched. This term is further exemplified by groups such as methyl, ethyl, n-propyl, isopropyl, isobutyl, t-butyl, pentyl, and cyclopentyl. Alkyl groups can either be unsubstituted or substituted with one or more substituents, e.g., halogen, alkyl, alkoxy, hydroxyl, carboxyl, aryloxy, aryl, arylalkyl, heteroaryl, amino, alkylamino, dialkylamino, or other functionality. The term lower alkyl means the chain includes 1-10 carbon atoms. Lower alkyl groups can also be unsubstituted or substituted.

Analogue, Derivative or Mimetic: An analogue is a molecule that differs in chemical structure from a parent compound, for example a homolog (differing by an increment in the chemical structure, such as a difference in the length of an alkyl chain), a molecular fragment, a structure that differs by one or more functional groups, a change in ionization. Structural analogues are often found using quantitative structure activity relationships (QSAR), with techniques such as those disclosed in Remington (*The Science and Practice of Pharmacology*, 19th Edition (1995), chapter 28). A derivative is a biologically active molecule derived from the base structure. A mimetic is a molecule that mimics the activity of another molecule, such as a biologically active molecule. Biologically active molecules can include chemical structures that mimic the biological activities of a compound.

Antibiotic: An antimicrobial agent that inhibits bacterial growth (bacteriostatic) or kills bacteria (bacteriocidal). Some classes of antibiotics are produced by microorganisms or plants, or obtained from other natural sources.

Antimicrobial agent: Any agent that kills microorganisms or suppresses their growth. This term includes both microbiocidal agents, as well as those agents that inhibit growth or maintain stasis of target microorganisms, such as bacteria and fungi.

Aromatic or aryl compounds typically are unsaturated, cyclic hydrocarbons having alternate single and double bonds. Benzene, a 6-carbon ring containing three double bonds, is a typical aromatic compound. Aryl compounds and aryl groups (e.g., as part of a larger molecule) can be unsubstituted or substituted with one or more substituents, e.g., halogen, alkyl, alkoxy, hydroxyl, carboxyl, aryloxy, aryl, arylalkyl, heteroaryl, amino, alkylamino, dialkylamino, or other functionality.

Bioassay: Measurement of the concentration or potency of a substance by its effect on living cells or tissues.

Pathogen: An agent capable of causing disease in a subject. The term "pathogen" typically refers to infectious organisms, including bacteria, viruses, and fungi.

Pharmaceutically acceptable carriers: Conventional pharmaceutically acceptable carriers are useful for practicing the methods and forming the compositions disclosed herein. *Remington's Pharmaceutical Sciences*, by E. W. Martin, Mack Publishing Co., Easton, Pa., 15th Edition, 1975, describes examples of compositions and formulations suitable for pharmaceutical delivery of the chrysophaentin compounds herein disclosed.

In general, the nature of the carrier will depend on the particular mode of administration being employed. For example, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Subject: An animal or human subjected to a treatment, observation or experiment.

Substituent: An atom or group of atoms that replaces another atom in a molecule as the result of a reaction. The term "substituent" typically refers to an atom or group of atoms that replaces a hydrogen atom on a parent hydrocarbon chain or ring.

Substituted: A fundamental compound, such as an aryl or aliphatic compound, or a radical thereof, having coupled thereto, typically in place of a hydrogen atom, a substituent. For example, substituted aryl compounds or substituents may have an aliphatic group coupled to the closed ring of the aryl base, such as with toluene. Again solely by way of example and without limitation, a long-chain hydrocarbon may have a substituent bonded thereto, such as one or more halogens, an aryl group, a cyclic group, a heteroaryl group or a heterocyclic group.

Therapeutically effective amount: A quantity or concentration of a specified compound or composition sufficient to achieve a desired effect in a subject being treated. For example, this may be the amount of a chrysophaentin compound or composition necessary to prevent, inhibit, reduce or relieve a bacterial infection in a subject. Ideally, a therapeutically effective amount of a compound or composition is an amount sufficient to prevent, inhibit, reduce or relieve bacterial infection without causing a substantial cytotoxic effect on non-microbial cells. However, the therapeutically effective amount of a chrysophaentin compound or composition will be dependent on the subject being treated, the severity of the affliction, and the manner of administration of the therapeutic composition.

Treating or treatment: With respect to disease, either term includes (1) preventing the disease, e.g., causing the clinical symptoms of the disease not to develop in an animal that may be exposed to or predisposed to the disease but does not yet experience or display symptoms of the disease, (2) inhibiting the disease, e.g., arresting the development of the disease or its clinical symptoms, or (3) relieving the disease, e.g., causing regression of the disease or its clinical symptoms.

II. FtsZ Protein

A relatively new target in antimicrobial drug discovery programs is the bacterial cell division protein FtsZ. Not only is this protein essential for bacterial cell division, but it is highly conserved among almost all bacteria making it an attractive antimicrobial target. FtsZ, which is encoded by the ftsZ gene, is not found in mammalian cells and therefore represents a specific target for antimicrobial agents. Agents that inhibit FtsZ therefore are able to specifically affect microbial cells (such as bacteria) without adversely affecting cell division in mammals being treated for an infection.

Most prokaryotes divide by binary fission, in which one cell divides into two daughter cells. During growth of rod-shaped bacteria (e.g., *E. coli* and *Bacillus subtilis*), a septum forms at the midpoint of the dividing cell, and subsequently pinches off to produce two progeny cells. The septum is formed by inward growth of cytoplasmic membrane and cell wall material that invaginates from opposite directions at the cell's central plane. During the early stages of cell division, FtsZ, a structural homolog of the eukaryotic cytoskeletal protein tubulin, is the first protein to move to the division site. FtsZ undergoes guanosine 5-triphosphate (GTP)-dependent polymerization to form protofilaments that assemble into a dynamic and contractile structure known as the Z-ring, marking the plane of cell division. The Z-ring is thought to form a scaffold for recruitment of other key cell division proteins. Inhibition of proper FtsZ assembly can block cell division by preventing Z-ring formation, ultimately leading to bacterial cell death.

FtsZ is found in most bacteria, although some L-form bacteria that lack a cell wall do not require FtsZ for division. FtsZ is also found in archaea, chloroplasts and some mitochondria. FtsZ may function as a universal prokaryotic division protein, and is the only cell division protein common to both *Mycoplasma genetalium* (the smallest bacteria and possessing a minimal genome) and more complex bacteria, such as *E. coli*.

FtsZ is capable of binding to GTP and exhibits GTPase activity. In vivo, FtsZ polymerizes in a GTP-regulated manner to form filaments, which assemble into a ring, called the Z-ring, around the longitudinal midpoint, or septum, of the cell. While GTP-hydrolysis is not essential to the formation of filaments or division, mutants lacking the GTPase domain form twisted and disordered septa, and the cells divide abnormally. (Bi et al., *Nature*, 354(3-5):161-164, 1991.) It is unclear whether FtsZ itself provides the physical contractile force that causes division or whether other proteins cause division. However, it is thought that a number of accessory proteins (e.g., ZipA, FtsA, FtsW, FtsK, and FtsQ) may be involved in ring assembly and stabilization of the Z-ring, and may participate in the division event.

FtsZ can assemble into protofilaments, two-dimensional sheets, and protofilament rings in in vitro studies. FtsZ and tubulin, FtsZ's eukaryotic analogue, share substantial sequence identity of their N-terminal GTP-binding domains, although the overall sequence identity is less than 20%. (Burns, *Nature*, 391:121-123, 1998.) Structural alignments show the N-terminal domains of FtsZ and tubulin are nearly identical in structure. (Erickson, *Trends in Cell Biology*, 8:133-137, 1998.)

In eukaryotic pathogens, cell division has been a productive target for finding drugs to combat infection or uncontrolled cell proliferation. Many of the drugs target microtubules. Because FtsZ plays an essential role in prokaryotic cell division, is widely conserved amongst bacteria, and is absent in the mitochondria of higher eukaryotes, it is an attractive target for developing drugs to combat bacterial pathogens. Although efforts to identify inhibitors of FtsZ have increased rapidly in recent years, the target remains underexploited. Compounds reported to inhibit the function of FtsZ include the natural products viiriditoxin, totarol, berberine, sanguinarine, and cinnamaldehyde, together with synthetic inhibitors such as PC190723, zantrins, and OTBA (3-{5-[4-oxo-2-thioxo-3-(3-trifluoromethyl-phenyl)-thiazolidin-5-ylidenemethyl]-furan-2-yl}-benzoic acid).

III. Chrysophaentins

Marine organisms have been found to be an excellent source to search for new FtsZ inhibitors because of their unique structures and strong antimicrobial activity. It was discovered that a methanol extract of the yellow alga *Chrysophaeum taylori* strongly inhibited the growth of *Staphylococcus aureus*, MRSA, *Enterococcus faecium*, and vancomycin-resistant *E. faecium* (VREF). Bioassay and LC-MS guided fractionation led to the isolation of eight novel polyhalogenated, polyoxygenated bisdiarylbutene ether macrocycles termed chrysophaentins A-H, hereinafter chrysophaentins 1-8, respectively. Their planar structures were determined by extensive spectroscopic methods including NMR and MS. With the exception of chrysophaentin 5, the structures are characterized by the presence of two polyhalogenated and polyoxygenated ω,ω'-diarylbutene chains linked through two ether bonds forming a macrocycle. Chrysophaentin 5 (compound 5) is an acyclic analogue containing only one ether bond linking the diarylbutene chains.

In some embodiments, the chrysophaentins are chrysophaentin antibiotics obtained by sequentially extracting lyophilized *Chrysophaeum taylori* with hexanes, chloroform, and methanol. The extracted chrysophaentins have antibacterial activity against at least *S. aureus*, *E. faecium*, and *B. subtilis*.

The chrysophaentins also include pharmaceutical salts of the compounds.

The structures of some chrysophaentins are represented by general formulas I, II and III:

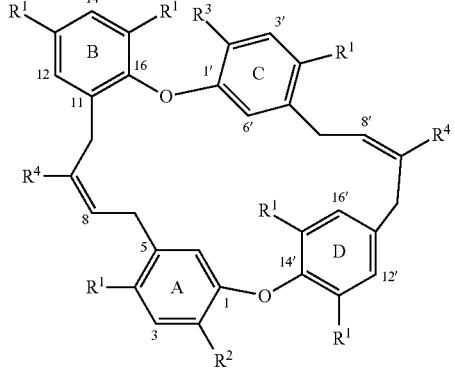

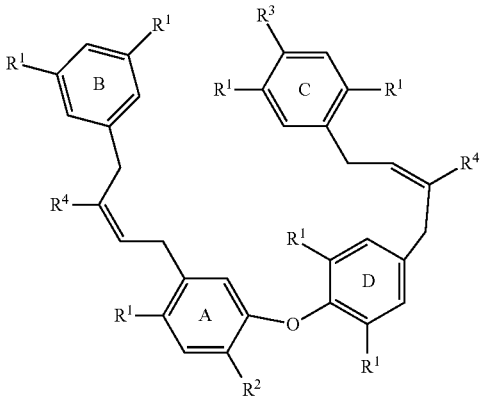

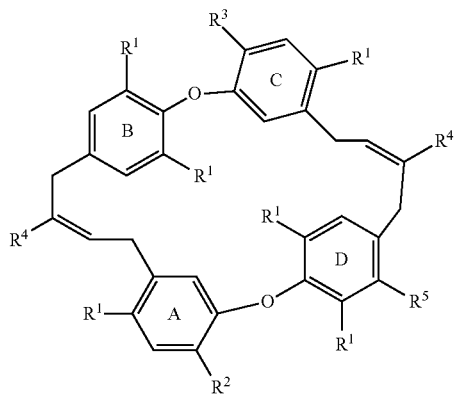

where each $R^1$ is independently hydrogen, hydroxyl, thiol, halogen, lower alkyl, lower alkoxy, or lower alkyl ester, and $R^2$, $R^3$, $R^4$, and $R^5$ are each independently hydrogen, hydroxyl, thiol, or halogen. In some embodiments, each $R^1$ is independently hydroxyl or lower alkyl ester; $R^2$, $R^3$ and $R^4$ are each independently halogen; and $R^5$ is hydrogen or halogen. In particular embodiments, $R^1$ is hydroxyl or acetate ($CH_3COO-$), $R^2$ and $R^3$ independently are chloro or bromo, $R^4$ is chloro, and $R^5$ is hydrogen or bromo, or any combination or subcombination thereof. Without being bound by any particular theory, it is thought that formula II may represent an intermediate, or transitional, structure between formulas I and III.

Certain embodiments of the chrysophaentins are represented by general formulas IV, V, and VI where $R^1$, $R^2$, $R^3$, and $R^5$ are independently selected from halogen, hydroxyl, or acetate. In particular embodiments $R^1$ is hydroxyl, $R^2$ and $R^3$ are chloro or bromo, and $R^5$ is hydrogen or bromo. Particular examples of this new class of antimicrobial agents are indicated below as compounds 1-8:

modified via acetylation to produce a synthetic chrysophaentin (compound 1a, where Ac=acetyl, —C(O)CH$_3$). The structures of compounds 1-8 and 1a are shown below:

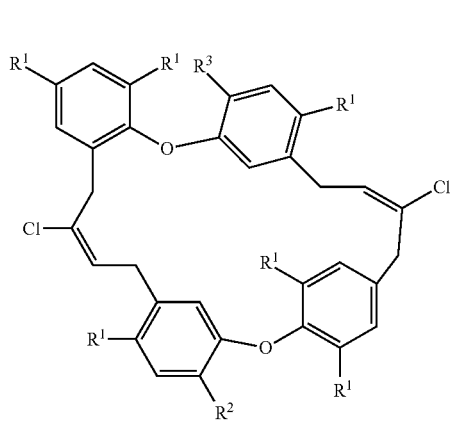

IV

1 $R^1$ = OH  $R^2$ = Cl  $R^3$ = Cl
1a $R^1$ = Ac  $R^2$ = Cl  $R^3$ = Cl
2 $R^1$ = OH  $R^2$ = Br  $R^3$ = Cl
3 $R^1$ = OH  $R^2$ = Cl  $R^3$ = Br
4 $R^1$ = OH  $R^2$ = Br  $R^3$ = Br

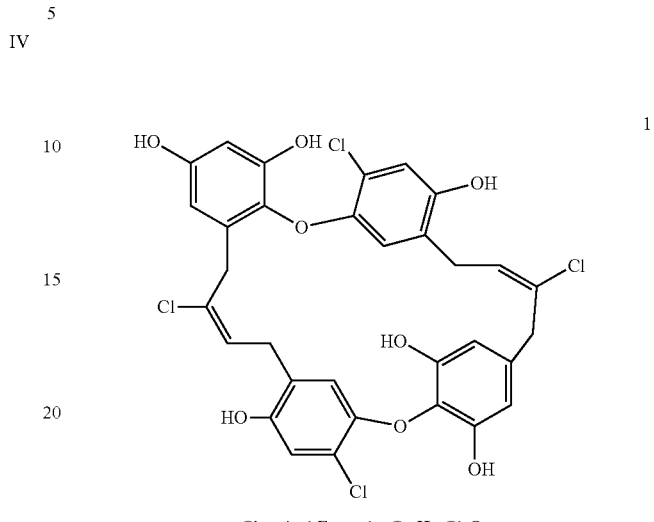

1

Chemical Formula: $C_{32}H_{24}Cl_4O_8$
Exact Mass: 676.02

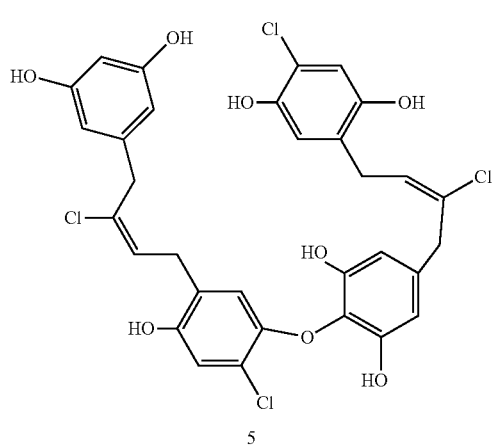

V

5

1a, hexaacetate of 1

Chemical Formula: $C_{44}H_{36}Cl_4O_{14}$
Exact Mass: 928.09

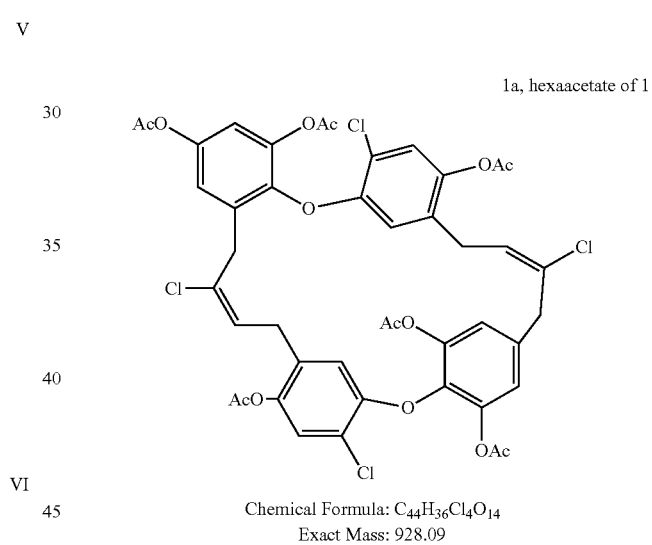

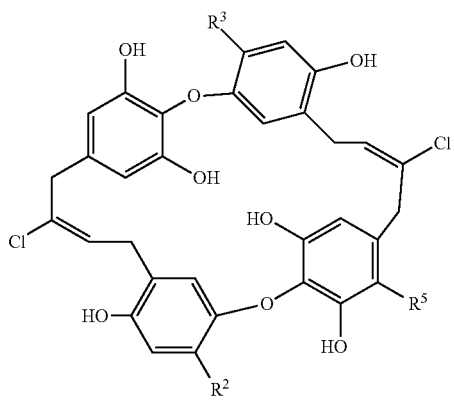

VI

6 $R^2$ = Cl  $R^3$ = Cl  $R^5$ = H
7 $R^2$ = Cl  $R^3$ = Br  $R^5$ = H
8 $R^2$ = Cl  $R^3$ = Cl  $R^5$ = Br

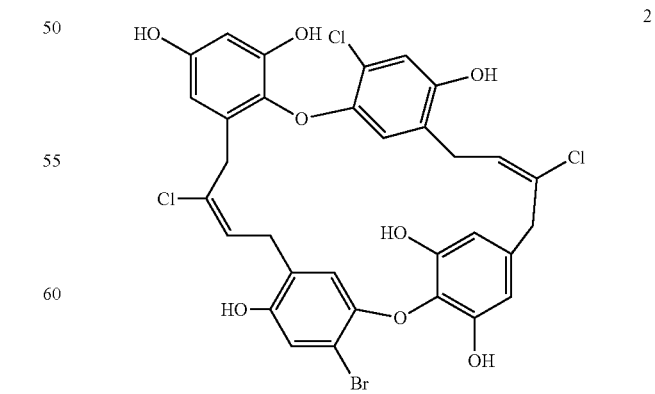

2

Chemical Formula: $C_{32}H_{24}BrCl_3O_8$
Exact Mass: 719.97

Eight chrysophaentins (compounds 1-8, respectively) having the substituent combinations shown above, were isolated from *Chrysophaeum taylori*. Additionally, compound 1 was

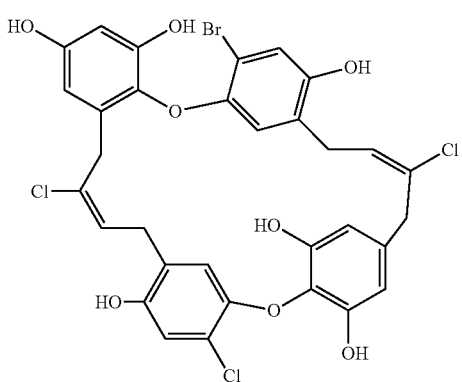

Chemical Formula: C₃₂H₂₄BrCl₃O₈
Exact Mass: 719.97

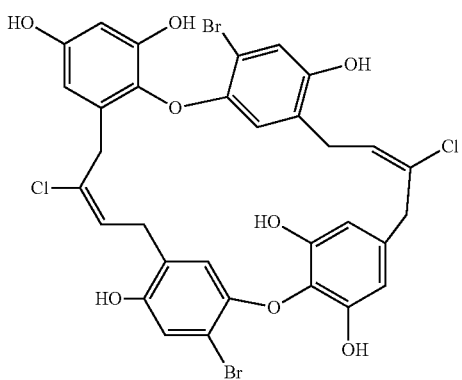

Chemical Formula: C₃₂H₂₄Br₂Cl₂O₈
Exact Mass: 763.92

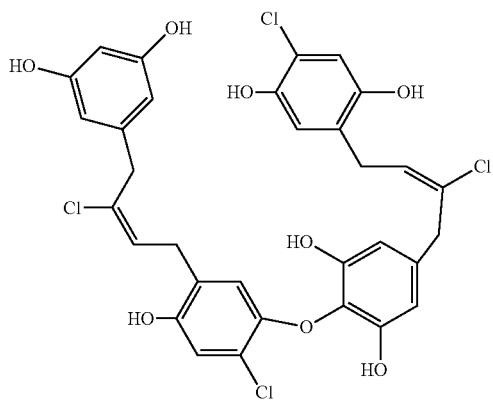

Chemical Formula: C₃₂H₂₆Cl₄O₈
Exact Mass: 678.04

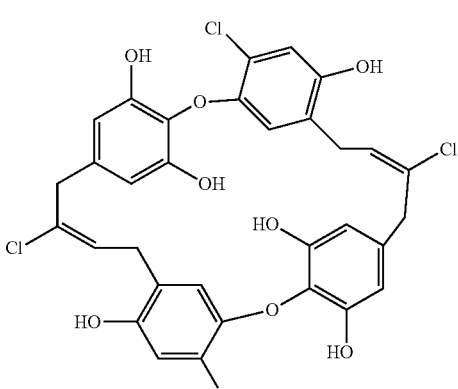

Chemical Formula: C₃₂H₂₄Cl₄O₈
Exact Mass: 676.02

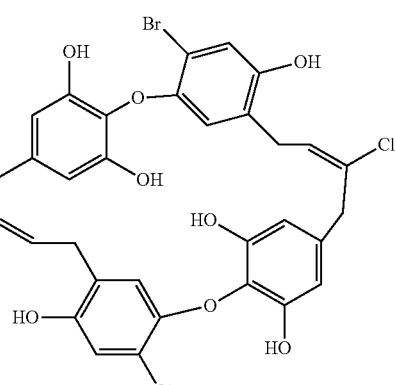

Chemical Formula: C₃₂H₂₄BrCl₃O₈
Exact Mass: 719.97

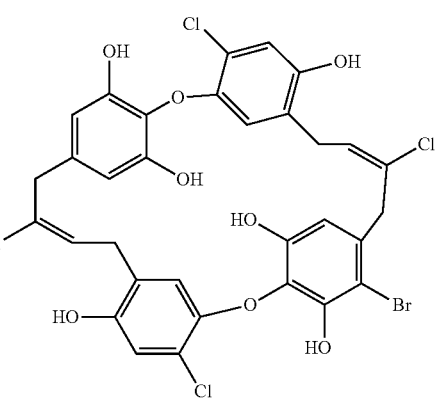

Chemical Formula: C₃₂H₂₃BrCl₄O₈
Exact Mass: 753.93

The antimicrobial activities and structures of the chrysophaentins were determined. Certain embodiments of the disclosed compounds possess antimicrobial activity against at least some clinically relevant bacteria. Structure-activity relationships suggest that when $R^1$ is hydroxyl, the compounds have increased antibiotic activity. Additionally, the presence of chlorines in the aromatic rings A and C, and the ortho position of the ether linkage respect to the alkyl substitution (i.e., position 11 in general formula I) in ring B were also correlated to stronger antibiotic potency.

In vitro results demonstrated that at least some embodiments of the disclosed compounds inhibit the GTPase activity and polymerization of FtsZ. Additionally, transmission electron microscopy, Saturation Transfer Difference (STD) NMR experiments and molecular docking models indicated that certain embodiments are capable of binding to FtsZ, competing with GTP for the same binding site. These results suggest that chrysophaentins may inhibit the hydrolysis of GTP by binding into the GTP pocket and, therefore, interfering with the early stages of bacterial cell division. In a working embodiment, at least one of the novel chrysophaentins, chrysophaentin 1, inhibited the GTPase and polymerization activity of FtsZ. Its mode of binding was also determined.

Further in vitro results showed that at least some embodiments of the chrysophaentins at antimicrobial concentrations do not inhibit tubulin, which is found in the microtubules of eukaryotic cells. For example, chrysophaentin 1 at a concentration 15 times greater than its $IC_{50}$ value for FtsZ inhibition had no effect on tubulin polymerization. In vitro testing also demonstrated that at least some embodiments of the disclosed compounds do not inhibit growth of mammalian cancer cell lines at concentrations as high as 50 µg/mL. Furthermore, at least some embodiments of the disclosed compounds do not exhibit cytotoxicity towards control mammalian cells (BSC-1) at concentrations as high as 100 µg/mL, which increases their potential as antibacterial drug candidates.

The results demonstrate that some embodiments of the disclosed compounds are capable of inhibiting FtsZ, thereby inhibiting bacterial cell division, while not affecting eukaryotic cell division. Thus, at least some embodiments of the disclosed compounds are promising candidates for a new class of antibiotics that are pathogen-selective and nontoxic when administered to a subject in need of antimicrobial treatment.

IV. Structure Determination

HR-ESI-MS of chrysophaentin 1 gave a molecular ion at m/z 675.0154 [M-H]⁻ consistent with a molecular formula of $C_{32}H_{24}Cl_4O_8$, including nineteen degrees of unsaturation. The presence of four chlorine atoms was confirmed by MS in-source experiments where fragmentation was induced by increasing the cone voltage from 30 to 125 eV. Fragment ions at m/z 649 [M-H—HCl]⁻, 603 [M-H-2HCl]⁻, 567 [M-H-3HCl]⁻, and 531 [M-H-4HCl]⁻ and their respective isotopic patterns clearly indicated the loss of four consecutive chlorine atoms. The IR spectrum of compound 1 showed bands at 3380 and 1680 cm⁻¹, implying the existence of hydroxyl and aromatic functionalities, respectively. The downfield region of the ¹H NMR spectrum of compound 1 in MeOH-d₄ contained signals for eight aromatic protons including two doublets at δ 6.18 (1H, d, J=2.8 Hz) and 6.30 (1H, d, J=2.8 Hz) corresponding to a tetrasubstituted benzene ring, a broad signal at δ 6.16 (2H, br s) suggesting the presence of two nearly equivalent protons, and four singlets at δ 6.179 (1H, s), 6.28 (1H, s), 6.81 (1H, s), and 6.84 (1H, s); as well as signals for two olefinic protons at δ 5.99 (1H, t, J=8.7 Hz) and 6.07 (1H, t, J=8.1 Hz). Thirty-two resonances were observed in the ¹³C NMR spectrum of 1, and the HSQC spectrum contained cross peaks ascribable to eight aromatic methine carbons (δ 103.8, 107.9, 109.1x2, 116.0, 116.7, 117.1, and 177.3), four benzyl methylene signals (δ 30.6, 30.4, 33.7, and 40.6), and two olefinic methines (δ 127.7 and 127.9).

Analysis of the 2D NMR data (HSQC, HMBC, COSY, and ROESY) of compound 1 led to the identification of two main fragments (I and II):

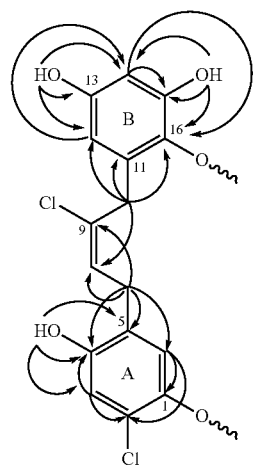

I

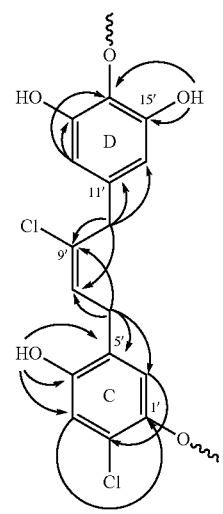

II

HSQC and HMBC correlations from the aromatic protons at δ 6.16-6.84 led to the construction of four independent tetrasubstituted benzene rings, A-D. Rings A and C each possessed chloro and alkyl substituents at positions 2 and 5, respectively, and two oxy substituents at positions 1 and 4. Rings B and D each contained three oxy substituents, with ring B displaying ortho-coupled AB-type proton signals and ring D displaying AA'-type signals. COSY data then correlated the olefinic triplet at δ 5.99 (H-8) to the benzylic methylene at δ 3.23 (2H, d, J=8.7 Hz, H-7) and in turn, diagnostic HMBC correlations observed from these methylene protons to the carbon resonances at δ 116.0 (C-6), 126.7 (C-5), 150.4 (C-4), and 134.7 (C-9), and from the benzylic methylene protons at δ 3.39 (2H, br s, H-10) to the carbon resonances at δ 107.9 (C-12), 133.0 (C-11), 135.9 (C-16), and 127.7 (C-8), linked rings A and B via a 2-butene chain. The partial structure I was completed by assigning the deshielded quaternary carbon at δ 134.7 (C-9) to a chlorinated alkene. The geometry of the C8/C9 double bond was established as E on the basis of strong ROEs between the methylene protons H-7 and H-10. Thus, the partial structure I was characterized by the presence of two aryl rings ω,ω'-linked to an (E)-2-chlorobut-2-ene moiety.

2D NMR data corresponding to fragment II closely resembled those of I, and indicated that the partial fragment II also contained an ω,ω'-diarylalkene unit. In particular, a set of long-range correlations from the methylene protons at δ 3.57 (2H, br s, H-10') to the aromatic carbons at δ 109.1 (C-12' and C-16'), to the chlorinated olefinic quaternary carbon at δ 134.4 (C-9'), and to the olefinic methine carbon at δ 127.9 (C-8') linked ring D to the 2-butene moiety as shown. Additional HMBC correlations from the remaining benzylic methylene at δ 3.28 (2H, d, J=7.9 Hz, H-7') to the aromatic carbons at δ 116.7 (C-6') and 150.7 (C-4'), and to the olefinic carbons C-8' and C-9', linked ring C to the remainder of fragment II, and ROEs between the methylene protons H-7' and H-10' indicated an E geometry at the C-8'/C-9' double bond of fragment II (see Table 1, Example 1).

Inspection of the partial fragments I and II revealed that together they contained eighteen of the required nineteen degrees of unsaturation, and only eighteen of the twenty-four protons were attached to carbons. Consequently there had to be six hydroxyl groups and fragments I and II had to be connected through two ether linkages to satisfy the unsaturation index and molecular formula of 1. This was further corroborated by acetylation of compound 1, which yielded the hexaacetate compound 1a.

The $^1$H NMR spectrum of compound 1 recorded in DMF-$d_7$ displayed excellent line shape and resolution for the resonances ascribable to six hydroxyl protons at δ 9.40-10.1. In fact, HMBC and ROESY correlations from these hydroxyl protons allowed unambiguous assignment of the positions of the hydroxyl groups and ether linkages connecting fragments I and II. Long-range correlations from the hydroxyl proton at δ 9.90 (1H, s, OH-4) to the carbon resonances at δ 116.1 (C-3), 125.6 (C-5), and 149.7 (C-4), and from the hydroxyl resonance at δ 10.1 (1H, s, OH-4') to the carbon resonances at δ 116.0 (C-3'), 125.9 (C-5'), and 150.4 (C-4'), showed that the ether bonds must occur at C-1 and C-1' in rings A and C, respectively. Similarly, HMBC correlations from the hydroxyl protons at δ 9.41 (1H, s, OH-13) and δ 9.58 (1H, s, OH-15) to carbons corresponding to C-12-C-14 ($δ_C$ 106.7, 155.5, 103.1) and C-14-C-16 ($δ_C$ 103.1, 150.7, 134.9), respectively (see Table 1, Example 1), provided clear evidence of their respective locations at C-13 and C-15, as well as positioning the ether bond at C-16 in ring B. The chemical equivalency of the aromatic protons H-12' and H-14' (δ 6.25, br s), and of the hydroxyl protons OH-13' and OH-15' (δ 9.44, s) suggested a symmetrical arrangement of the substituents on ring D and positioning the ether linkage at C-14. This was further corroborated by HMBC correlations between protons OH-13'/OH-15' and carbon resonances at δ 151.2 (C-13'/C-15') and 128.6 (C-14'). Finally, connectivities between fragments I and II were assigned from a ROESY spectrum. In particular, ROEs between OH-15' and H-6 (δ 6.39) required C-14' of ring D to be connected to C-1 of ring A via an ether bond, while an ROE between H-6' (δ 6.51) and methylene protons H-10 (δ 3.57) suggested rings B and C were linked by the second ether bond at C-16 and C-1', respectively. Therefore the structure of chrysophaentin 1 was established as a macrocyclic dimer composed of two ω,ω'-diaryl-2-chlorobut-2-ene moieties linked through two ether bonds in an asymmetric fashion.

To view the conformational features of chrysophaentin 1, a 3D model was constructed via a full exploration of the conformational space of chrysophaentin 1 by performing molecular dynamics calculations at different temperatures (300 K, 500K, 700K/50 ns) using the AMBER force field in the program MacroModel. Each of the obtained conformations was minimized with the Polak-Ribier Conjugate Gradient (PRCG) algorithm. The global minimum energy conformer is shown in FIG. 1 where the interproton distances observed are in good agreement with the ROESY data. In particular the distances measured between protons H-6/H-10 (2.5 Å), H-10/H-12 (2.8 Å), H-6'/H-8' (2.6 Å), H-7'/H-10' (2.3 Å), and H-7/H-10 (3.2 Å) were consistent with the strong ROEs observed for each of these proton pairs.

HR-ESI-MS and MS in-source experiments showed chrysophaentin 2 (compound 2) and chrysophaentin 3 (compound 3) to possess the same molecular formula, $C_{32}H_{24}BrCl_3O_8$ (m/z 718.9655 [M-H]$^-$ and 718.9650 [M-H]$^-$), while that of chrysophaentin 4 (compound 4) was assigned as $C_{32}H_{24}Br_2Cl_2O_8$ (m/z 762.9168 [M-H]$^-$). The 2D NMR data (HSQC, HMBC, COSY, and ROESY) for compounds 2-4 were almost superimposable with those of compound 1. Analysis of the 1D and 2D NMR data showed compounds 2 and 3 to be the 2- and 2'-brominated analogues of compound 1, while compound 4 was shown to be the 2,2'-dibrominated analogue.

The HR-ESI-MS of chrysophaentin 5 (compound 5) showed a pseudomolecular ion peak at m/z 677.0317 [M-H]$^-$ corresponding to a molecular formula of $C_{32}H_{26}Cl_4O_8$ (calculated for $C_{32}H_{25}Cl_4O_8$, 677.0304) that differed from compound 1 by addition of two hydrogen atoms and included eighteen degrees of unsaturation, or one less than compound 1. The $^1$H NMR spectrum of compound 5 in MeOH-$d_4$ (see Table 4, Example 1) showed signals corresponding to four benzyl methylenes at δ 3.32 (2H, d, J=7.9 Hz)), 3.41 (2H, d, J=7.8 Hz), 3.52 (2H, br s), and 3.69 (2H, br s), and two olefinic triplets at δ 5.88 (1H, t, J=7.9 Hz) and 5.73 (1H, t, J=7.9 Hz), suggesting the presence of two sets of 2-butene chains. The aromatic region of the $^1$H NMR spectrum also revealed four downfield singlets at δ 6.44 (1H, s), 6.70 (1H, s), 6.74 (1H, s), and 6.84 (1H, s), three meta-coupled protons belonging to an AA'B spin system at δ 6.13 (1H, d, J=1.8 Hz) and 6.16 (2H, d, J=1.8 Hz) corresponding to a 1,3,5-trisubstituted benzene ring, and two singlet protons belonging to an AA' spin system at δ 6.41 (2H, s) corresponding to a symmetrical tetrasubstituted ring. The 2D NMR data of compound 5 were consistent with two sets of two aryl rings ω,ω'-linked to an (E)-2-chlorobut-2-ene chain and closely resembled that of compound 1; however there were some significant differences in the chemical shifts of protons and carbons of rings B and C. The most notable difference appeared at C-16 (ring B) where the oxygenated substitution in compound 1 was absent in compound 5. Moreover, the $^1$H NMR spectrum of compound 5 in DMF-$d_7$ showed signals corresponding to seven hydroxyl protons (one more than 1) at δ 9.34 (2H, s), 9.52 (1H, s), 9.55 (1H, s), 9.60 (2H, s), and 9.82 (1H, s). Together these data suggested that the two diarylalkene moieties in compound 5 were linked via one ether bond only. At last, HMBC correlations of the hydroxylated protons located the seven hydroxyl groups at C-4, C-13, C-15, C-1', C-4', C-13', and C-15' and thereby demonstrated that there had to be an ether bond linking C-1 in ring A to C-14' in ring D, completing the structure of chrysophaentin 5. Thus, chrysophaentin 5 is an acyclic bis-diarylbutene having a 1-14' ether bond.

The total ion chromatogram (TIC) obtained from the LC-MS also contained compounds 6-7 with identical masses to compounds 1-3, but eluting at considerably longer retention times. Among this group, chrysophaentin 6 eluted from the C-12 HPLC column after chrysophaentin 1 (compound 1 $t_R$=28.0 min; compound 6 $t_R$=41.3 min) and its molecular formula was determined to be $C_{32}H_{24}Cl_4O_8$ by HR-ESI-MS (675.0140 [M-H]$^-$, calculated for $C_{32}H_{23}Cl_4O_8$, 675.0147), indicating that compound 6 was an isomer of compound 1. The $^1$H NMR and HSQC spectra of compound 6 displayed characteristic signals for a single ω,ω'-diarylbutene moiety, including two benzylmethylenes ($δ_H$ 3.35, $δ_C$ 31.0; $δ_H$ 3.54, $δ_C$ 39.8), one olefinic triplet ($δ_H$ 5.89, $δ_C$ 127.2), and four aromatic singlets ($\delta_H$ 6.23, $\delta_C$ 110.0×2; $\delta_H$ 6.42, $\delta_C$ 115.1; $\delta_H$ 6.90, $\delta_C$ 117.3). Furthermore, HMBC and COSY experiments led to the identification of a 2-chlorobut-2-ene moiety linked in position 1 to a 2-chlorine-5-alkylbenzene-1,4-diol and in position 4 to a 5-alkylbenzene-1,2,3-triol. Overall these NMR data accounted for only half of the molecular formula of compound 6, indicating chrysophaentin 6 is a symmetrical dimer comprising two identical diarylalkenes linked through two ether bonds. Thus, the 2D NMR data clearly established that the structure of chrysophaentin 6 differed from that of compound 1 in the location of the ether bond in ring B. In chrysophaentin 6 the ether bond is para to the alkyl group, while in chrysophaentin 1 it is ortho. Connectivity was confirmed from an HMBC experiment ($^4J_{CH}$=2 Hz) showing a correlation between H-6 and C-14'. Finally, the geometry of the double bond at C-8/C-9 was established as E on the basis of ROE correlations observed between the methylenes H-7 and H-10. Thus the structure of chrysophaentin 6 was established to be the symmetrical macrocyclic ether, compound 6.

Chrysophaentin 7 (compound 7) displayed a major ion peak at m/z 718.9620 [M-H]$^-$ corresponding to a molecular formula of $C_{32}H_{24}BrCl_3O_8$, and differed from the molecular formula of compound 6 by the replacement of chlorine with a bromine atom. Successively, comparison of the 2D NMR data of compound 7 to that of compound 6 determined that the bromine atom was located at the C-2' position. Chrysophaentin 8 (compound 8) was the most hydrophobic compound of this group of antibiotics eluting from the C-12 HPLC column at even higher retention times than compound 6 (compound 6 $t_R$=41.3 min; compound 8 $t_R$=50.5 min). Its molecular formula was assigned as $C_{32}H_{23}BrCl_4O_8$ (HR-ESI-MS m/z 752.9255 [M-H]$^-$), which was 78 amu higher than compound 6. Analysis of the 2D NMR data for compound 8 established chrysophaentin 8 to be the 12'-bromo-derivative of compound 6.

V. Antimicrobial Activity and Structure-Activity Relationships

Solid agar disk diffusion and microbroth dilution assays were used to evaluate the antimicrobial activities of compounds 1, hexaacetate 1a, and 4-8 toward clinically relevant, Gram-positive pathogens, including the drug-susceptible bacteria *Staphylococcus aureus, Bacillus subtilis* and *Enterococcus faecium*, and drug-resistant strains methicillin-resistant *S. aureus* (MRSA), multidrug-resistant *S. aureus* (MDRSA), and vancomycin-resistant *E. faecium* (VREF) (see Table 7, Example 2). Initial disk diffusion assays showed that compounds 1, 4-6, and 8 inhibited the growth of all strains at loads ranging from 2-25 µg/disk. In both assay formats, chrysophaentin 1 (compound 1) was the most potent antibiotic giving respective minimum inhibitory concentrations ($MIC_{50}$) of 1.8±0.6, 1.5±0.7 µg/mL, and 1.3±0.4 µg/mL against *S. aureus*, MRSA, and multidrug-resistant *S. aureus* (MDRSA), respectively; 3.8±1.9 and 2.9±0.8 µg/mL toward *E. faecium* and VREF in microbroth dilution assays; and 10 mm zones of inhibition at 2 µg/disk for *S. aureus*, MRSA, *E. faecium*, and VREF. Chrysophaentins 6 and 8 (compounds 6 and 8) were the next most potent compounds with $MIC_{50}$ values of 4-6 µg/mL toward *S. aureus* and MRSA, and ~9.5 µg/mL against VREF (see Table 7, Example 2).

These screening results provided insight into structure-activity relationships for the chrysophaentins. The hexaacetate derivative of chrysophaentin 1 (compound 1a) was inactive at loads as high as 25 µg/disk indicating that the hydroxyl groups have a significant role in the antimicrobial activity of compound 1. The weaker potency of chrysophaentin 4 compared to chrysophaentin 1 indicated that chlorine on phenyl rings A and C affects antimicrobial activity since replacement with bromines results in an approximate 12-fold decrease in $MIC_{50}$ values toward all four strains. The acyclic metabolite chrysophaentin 5 was also found to be inactive toward *E. faecium* and VREF at concentrations as high as 25 µg/mL, and showed significantly higher $MIC_{50}$ values towards *S. aureus* and MRSA when compared to the chlorinated cyclic bisdiarylbutene ethers, compounds 1 and 6, establishing that the macrocyclic structure contributes to enhanced antimicrobial efficacy. Among the symmetrically linked dimers 6 and 7, the tetrachloro compound 6 was at least 3× more potent than compound 7, which differs only by replacement of a chlorine atom on ring C by bromine. With regard to the respective arrangements of the two diaryl butene ether units, comparison of the antibacterial activities of the tetrachlorinated macrocycles 1 and 6 shows chrysophaentin 1 to be 3-5 times more potent than chrysophaentin 6, indicating the positions of the ether linkages relative to the 2-butene units affect activity. Specifically, the ortho-linked chrysophaentin 1 is more potent than the para-linked chrysophaentin 6.

To assess specificity as an antimicrobial agent, chrysophaentin 1 was evaluated for cytotoxicity against the human colon tumor cell line HCT-116, the murine leukemia cell line P388, and a control mammalian cell line BSC-1. Interestingly, chrysophaentin 1 did not inhibit the growth of any of the tumor cell lines at concentrations as high as 50 µg/mL, and did not show cytotoxicity toward the control cells at concentrations as high as 100 µg/mL. These results indicate specificity of antimicrobial (such as antibacterial) activity and beneficial therapeutic indices.

VI. Screening Assays for FtsZ Inhibitors

The bacterial cytoskeletal protein FtsZ is a GTPase that plays a central role in bacterial cell division. At the time of replication, FtsZ localizes to the mid cell and undergoes GTP-dependent polymerization to form a dynamic and contractile structure known as the Z-ring, which marks the future plane of cell division. Inhibition of proper FtsZ assembly can block cell division by preventing Z-ring formation, ultimately leading to bacterial cell death. Assays that are suitable for screening compounds for FtsZ inhibitory activity include an in vitro colorimetric assay that measures production of inorganic phosphate upon FtsZ-mediated hydrolysis of GTP to GDP+Pi, and transmission electron microscopy visualization of in vitro GTP-dependent polymerization.

Chrysophaentin 1 was tested for its ability to inhibit recombinant FtsZ in vitro. A GTPase assay demonstrated that chrysophaentin 1 inhibited the GTPase activity of FtsZ in a dose-dependent manner with an $IC_{50}$ value of 6.7±1.7 µg/mL (Example 3 and FIG. 8).

Figure 2:
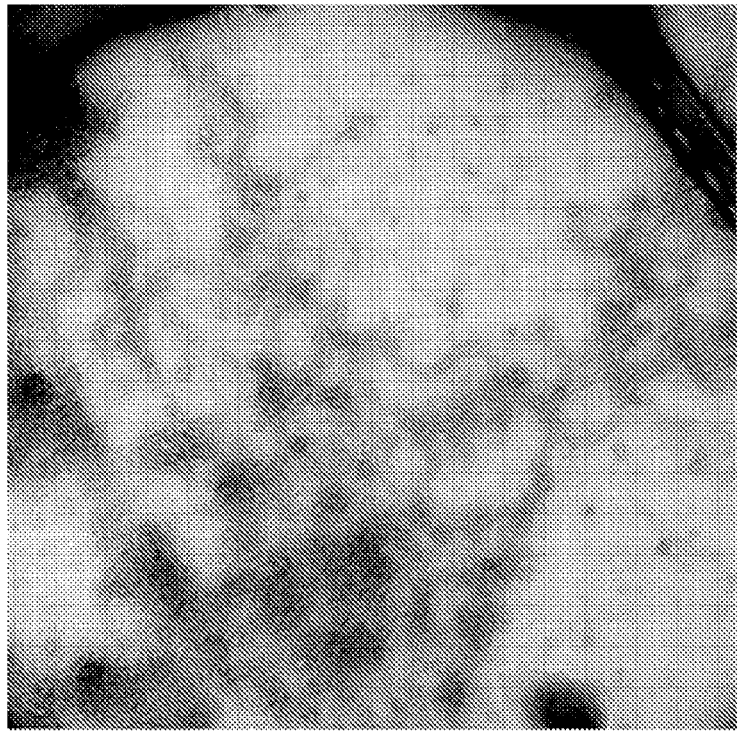
FIG. 2 is a transmission electron micrograph of FtsZ in the presence of GTP.

Transmission electron microscopy was utilized to visualize the effects of compound 1 on GTP-dependent polymerization of FtsZ. (Example 3 and FIGS. 2-3.) Upon addition of GTP (1 mM), FtsZ (6 µM) undergoes polymerization to form a network of protofilaments as shown in FIG. 2. In contrast, in the presence of 50 µM chrysophaentin 1 (FIG. 3), polymerization was inhibited. Upon viewing the entire grid, not a single protofilament was visualized; instead small protein aggregates of non-polymerized FtsZ were seen. Thus, incubation of FtsZ with compound 1 prior to addition of GTP fully inhibited polymerization and protofilament formation. However, compound 1 has no effect on tubulin polymerization at concentrations as high as 150 µM (Example 3 and FIG. 9).

Together these results demonstrate that chrysophaentin 1 is a new FtsZ inhibitor that exhibits at least a 15-fold selectivity for FtsZ over tubulin.

Interestingly, chrysophaentin 1 inhibits the growth of multiple bacterial strains with $MIC_{50}$ values that are considerably lower than the in vitro $IC_{50}$ values observed in GTPase assays. This phenomenon has been observed for other FtsZ inhibitors. Because formation of the Z-ring is an initial step in bacterial cell division, this differential activity has been attributed to amplification of the effect of inhibiting FtsZ polymerization. Similar effects are observed with microtubule inhibitors where micromolar concentrations are required for in vitro inhibition of tubulin polymerization, while nanomolar concentrations disrupt microtubule assembly in vivo. (Jordan et al., *Nat. Rev. Cancer,* 4:253, 2004.)

VII. Characterization of Chrysophaentin 1 Binding to FtsZ by STD NMR

To identify the regions of chrysophaentin 1 involved in FtsZ binding, Saturation Transfer Difference (STD) NMR spectra of compound 1 in the presence of recombinant FtsZ were recorded. Samples typically contained a 100-fold excess of chrysophaentin 1 relative to FtsZ with respective concentrations of 1.5 mM and 15 µM.

Figure 4:
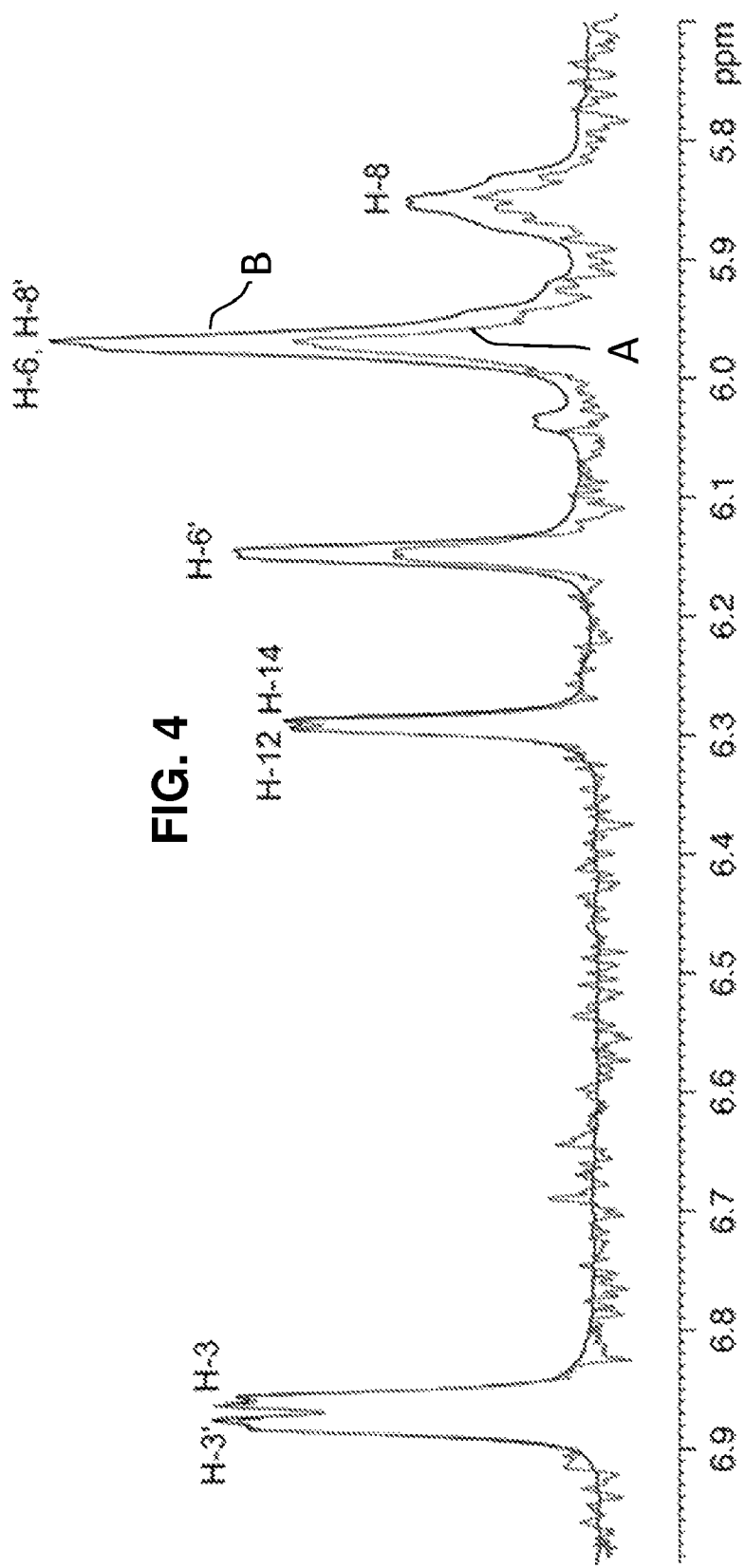
FIG. 4 depicts reference and STD NMR difference spectra of chrysophaentin 1 complexed with FtsZ.

An expansion of a representative difference spectrum (A) and control spectrum (B) is shown in FIG. 4 to include strongly enhanced and non-overlapping aromatic and olefinic protons of compound 1. Normalization of the signal/s of greatest intensity (δ 6.85) in the difference spectrum A to those of the reference spectrum B showed signals for the aromatic protons H-3 (100%), H-14 (100%), H-12 (100%), and H-3' (98%) to display the strongest enhancements, while the overlapped signals of the aromatic and olefinic protons H-6' and H-8 showed a combined enhancement of ~50%. Thus, when bound to FtsZ, the face of chrysophaentin 1 displaying protons H-3, H-14, H-12, and H-3' (rings A, B and C) is in closest proximity to the protein. Under the buffer conditions used to prepare the complexes, signals were not observed for the remaining two aromatic protons H-12' and H-14', both of which reside on ring D, in either $^1$H or STD NMR spectra.

Figure 5:
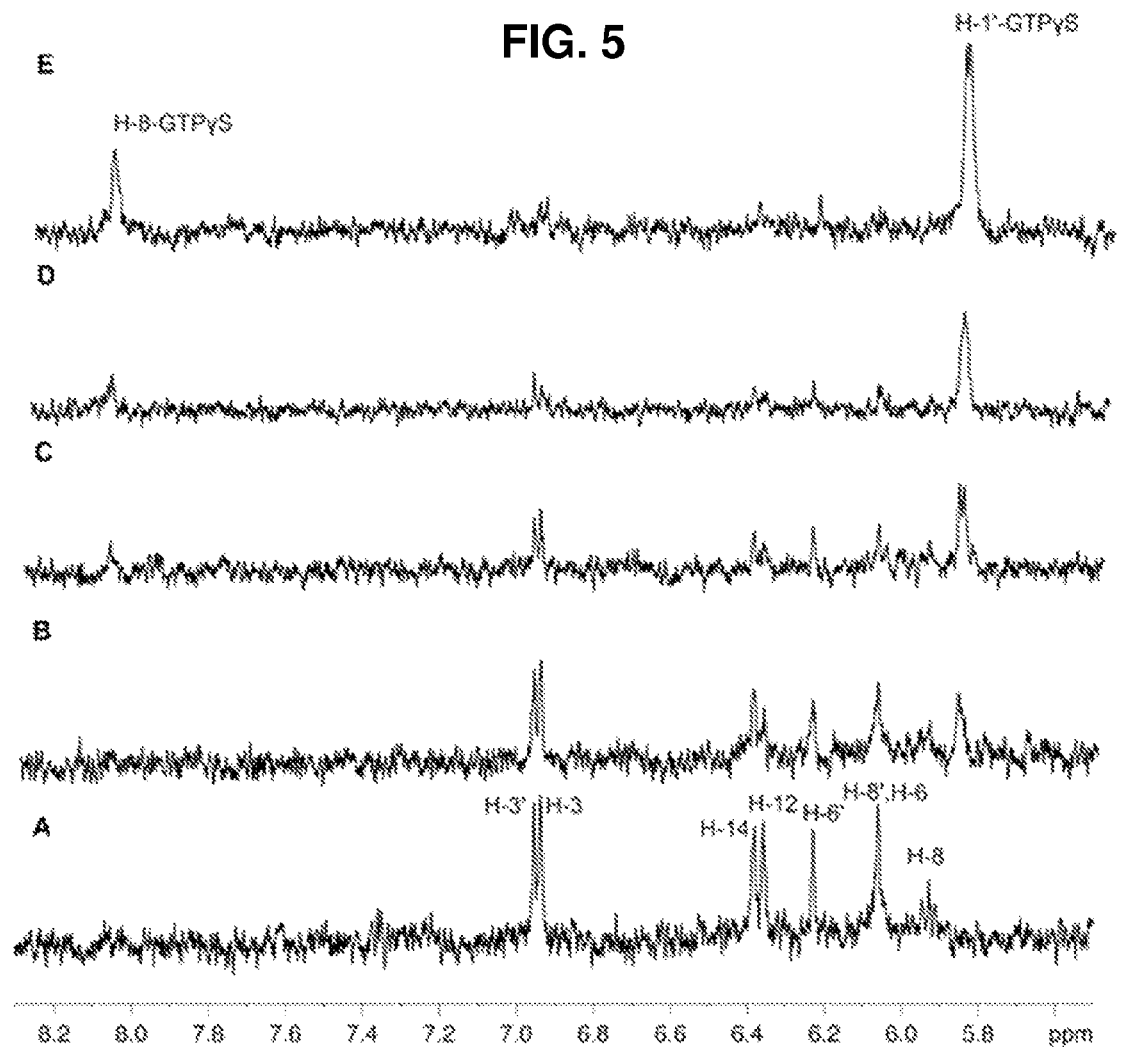
FIG. 5 is a series of STD NMR spectra of competition experiments for chrysophaentin 1 and GTPγS binding to FtsZ.

VIII. Chrysophaentin 1 Binds in and Competes with GTP for the GTP Binding Site of FtsZ Among those FtsZ inhibitors reported to date, inhibition of GTPase activity and/or polymerization can occur through multiple modes of binding to FtsZ. To gain insight into the mode of binding of chrysophaentin 1 to FtsZ, competition STD NMR experiments were performed. Increasing amounts of a non-hydrolyzable GTP analogue, guanosine 5'-O-3-thiotriphosphate (GTPγS), known to bind to the GTP binding site of FtsZ with high affinity, were added to a 100:1 complex of chrysophaentin 1:FtsZ. Spectra were recorded on samples containing 1.25 mM compound 1 in the presence of 12.5 µM FtsZ (FIG. 5). Difference spectra were monitored for a change in intensity of signals belonging to either chrysophaentin 1 or GTPγS during the titration. Spectrum A is an expanded $^1$H STD NMR spectrum of chrysophaentin 1 (1.25 mM) in the presence of FtsZ (12.5 µM). As seen in the spectral expansions showing the aromatic and olefinic region of the difference spectra (Spectrum B), addition of 0.5 equivalents of GTPγS (625 µM) resulted in an ~50% uniform decrease in intensity for signals belonging to compound 1. Moreover, a new STD NMR signal appeared at δ 5.84 (H-1'-GTPγS) that was assigned to the anomeric proton of the ribose of GTPγS (Spectrum B). Stepwise addition of another two equivalents of GTPγS to the complex (Spectra C and D, respectively) further diminished the signal intensities of compound 1 concomitant with steady increases in signal intensities for the anomeric and guanosine protons of GTPγS, H-1'$_{GTP\gamma S}$ and H-8$_{GTP\gamma S}$. As seen in Spectrum E, after addition of 3 equivalents of GTPγS relative to compound 1, signals for the natural product were imperceptible and had been replaced by those of GTPγS. Thus chrysophaentin 1 and GTPγS were shown to bind the GTP binding site of FtsZ in a competitive manner.

Several crystal structures of FtsZ in complex with GTPγS or GDP have been solved, providing a detailed view of the GTP binding site, which resides in the N-terminal domain and includes the conserved motif GGGTGTG that forms a large portion of the nucleotide binding site. To further evaluate the mode of binding of compound 1 to FtsZ, molecular docking studies were performed using the program Autodock Vina 1.0.3. Since a crystal structure of *E. coli* FtsZ was not available, a homology model was generated using the 2.1 Å crystal structure of *Pseudomonas aeruginosa* FtsZ, which displays the highest degree of conservation to *E. coli* FtsZ, as a template. Docking simulations were performed in two steps starting from the entire protein defined as target, where all reasonable docked models showed compound 1 to bind in or very near to the GTP binding site, followed by narrowing the grid search to the GTP binding site. To thoroughly assess the quality and observed binding modes of these calculations, we performed 25 docking runs where the majority of results showed compound 1 bound to FtsZ in the GTP binding site. Furthermore, the docked conformation and protein-ligand interactions observed for the fourth lowest energy binding model (−6.6 kcal/mol vs −7.0 kcal/mol for the global minimum energy binding mode) were entirely consistent with the STD NMR results.

Figure 6A:
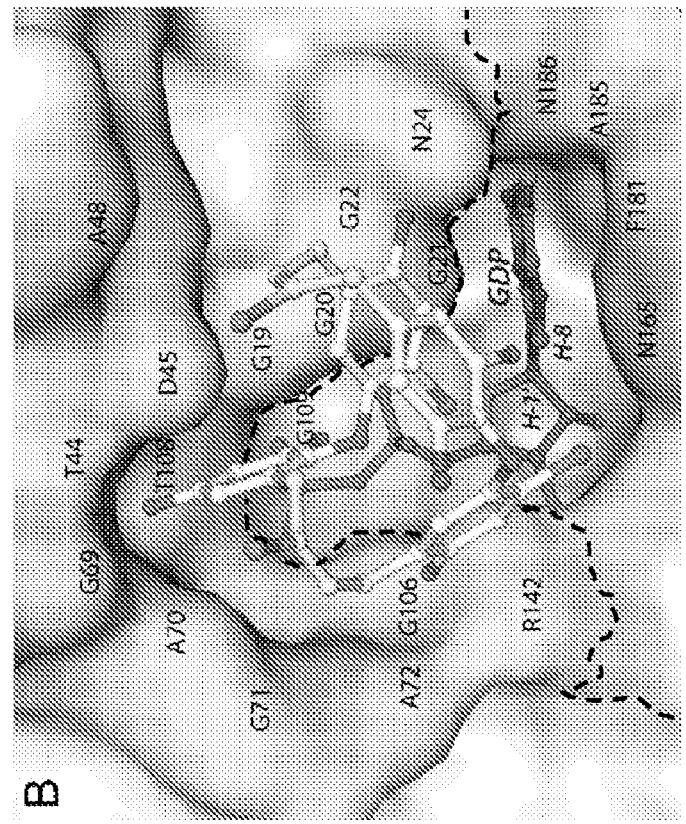
FIGS. 6A and 6B illustrate molecular docking of chrysophaentin 1 to FtsZ.
Figure 6B:
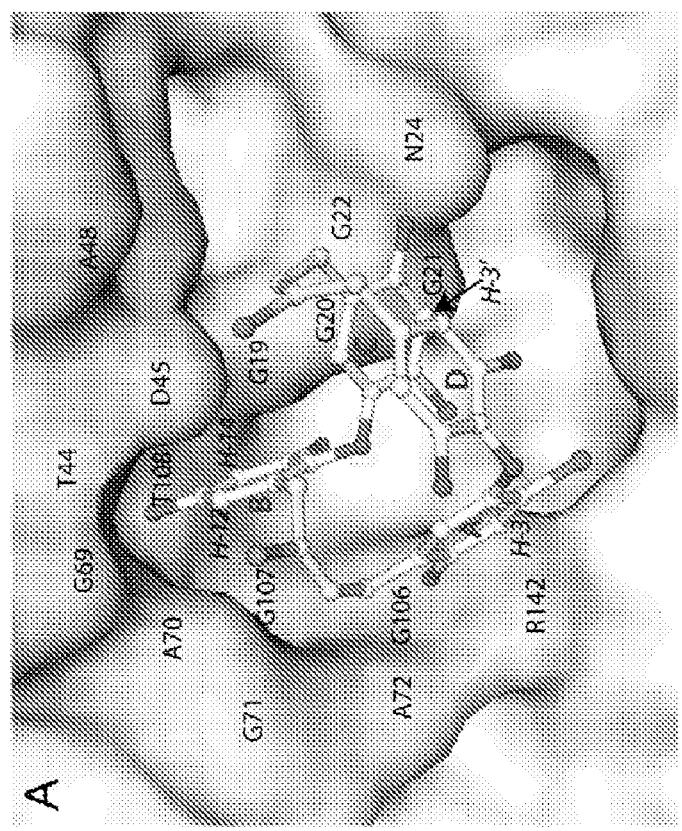

As shown in FIGS. 6A and 6B, the molecular docking of compound 1 to FtsZ suggests chrysophaentin 1 binds FtsZ in the GTP binding site. FIG. 6A illustrates a docked model of compound 1 bound to an *E. coli* FtsZ homology model; FtsZ is displayed as a white surface with surface residues located within 5 Å of compound 1 shaded gray; chrysophaentin 1 is shown in ball-and-stick representation with chlorine atoms (gray) located near G19, G107, just left of the letter "D" and in the lowermost left portion of the molecule. The remaining gray-colored atoms represent oxygen atoms. Protons displaying the strongest enhancements are labeled in italics.

FIG. 6B illustrates superposition of the docked model shown in FIG. 6A and GDP bound to *P. aeruginosa* FtsZ (Protein Data Bank accession number 1ofu.pdb) used to generate the *E. coli* homology model. GDP (dark gray and below chrysophaentin 1) is shown in a ball-and-stick representation, and surfaces of residues comprising the GTP binding site of FtsZ are below the dashed line superimposed on FIG. 6B. Docking was performed using the program Autodock Vina 1.0.3. In this docked model, chrysophaentin 1 occupies the triphosphate region of the GTP binding site and partially occludes the guanine binding site as well. The docked model places compound 1 within hydrogen bonding distances of the side chain or back-bone N and O atoms of Arg142, Gly20, Ala70, Asn43, Thr108, and Asn24. Furthermore, protons H-3, H-14, and H-12 which displayed the strongest STD enhancements (100%) are within van der Waal's distances of Arg142 (2.9 Å), Thr108 (2.4 Å), and Ala48 (2.2 Å), respectively; while H-3' of ring C (98% enhancement) is in close proximity to Gly20 (3.5 Å) and Gly21 (3.7 Å). Hydrophobic interactions were also observed for olefinic protons H-8 and Gly71 (3.5 Å), and H-8' and Ala48 (2.2 Å). Finally, the aromatic protons H-6 and H-6' that displayed much weaker enhancements (~50%) are positioned 4.5 Å or greater from the protein surface suggesting a smaller contribution to FtsZ binding.

When aligned with FtsZ sequences whose x-ray structures have been solved, all residues that are in contact with chrysophaentin 1 in the *E. coli* model reside within and would be predicted to form a portion of the GTP binding site. For instance, sequence alignments would indicate Gly20, Gly21, and Asn24 to be involved in base recognition; Asn43, Ala48, Ala70, and Thr108 to be involved in phosphate binding; and Arg142 to contribute to ribose recognition. These results support the theory that chrysophaentin 1 inhibits the GTPase activity and polymerization of FtsZ through binding to the nucleotide binding site in a competitive manner to GTP.

IX. Salts

Chrysophaentin compounds according to general formulas I, II, or III may be in the form of salts. Such salts include salts suitable for pharmaceutical uses ("pharmaceutically-acceptable salts"), salts suitable for veterinary uses, etc. Such salts may be derived from aqueous bases (e.g., aqueous metal hydroxides or metal hydrides), as is well-known in the art. Exemplary salts described herein are sodium salts, potassium salts, magnesium salts, and calcium salts, but generically any pharmaceutically acceptable salt may be used for methods described herein.

In one embodiment, the salt is a pharmaceutically acceptable salt. Generally, pharmaceutically acceptable salts are those salts that retain substantially one or more of the desired pharmacological activities of the parent compound and which are suitable for administration to humans. Pharmaceutically acceptable salts include salts formed when an acidic proton present in the parent compound is either replaced by a metal ion (for example, an alkali metal ion, an alkaline earth metal ion or an aluminum ion) or coordinates with an organic base (for example, ethanolamine, diethanolamine, triethanolamine, N-methylglucamine, morpholine, piperidine, dimethylamine, diethylamine, triethylamine, ammonia, etc.)

Chrysophaentin compounds according to general formulas I, II, or III, as well as the salts thereof, may also be in the form of solvates, for example hydrates, and N-oxides, as are well-known in the art.

X. Pharmaceutical Compositions and Methods of Treatment

This disclosure includes pharmaceutical compositions comprising at least one antimicrobial chrysophaentin. Some embodiments of the disclosed pharmaceutical compositions are capable of inhibiting bacterial growth (such as by inhibiting FtsZ) when applied to a bacterium. The pharmaceutical compositions may be applied to a bacterium in vitro, or the pharmaceutical composition may be formulated for use in human and/or veterinary medicine and may be applied to a bacterium in vivo by administering a therapeutically effective amount of the pharmaceutical composition to a subject.

Some embodiments of the pharmaceutical compositions include a pharmaceutically acceptable carrier and at least one active ingredient. Useful pharmaceutically acceptable carriers and excipients are known in the art. Active ingredients may comprise, for example, at least one chrysophaentin as described herein, or any combination of chrysophaentins as described herein. In addition, other medicinal or pharmaceutical agents, for example, with similar, related or complementary effects on the affliction being treated, may be included as active ingredients in pharmaceutical compositions.

Pharmaceutical compositions comprising embodiments of the disclosed chrysophaentin compounds may be manufactured by means of conventional mixing, dissolving, granulating, dragee-making, levigating, emulsifying, encapsulating, entrapping or lyophilization processes. The compositions may be formulated in a conventional manner using one or more physiologically acceptable carriers, diluents, excipients or auxiliaries which facilitate processing of the active compounds into preparations which can be used pharmaceutically.

The pharmaceutical compositions comprising one or more chrysophaentins may be formulated in a variety of ways depending, for example, on the mode of administration and/or on the location and type of disease to be treated. For example, such pharmaceutical compositions may be formulated as a pharmaceutically acceptable salt (e.g., a sodium or potassium salt), hydrate, or solvate of a disclosed chrysophaentin. As another example, parenteral formulations may comprise injectable fluids that are pharmaceutically and physiologically acceptable fluid vehicles such as water, physiological saline, other balanced salt solutions, aqueous dextrose, glycerol or the like. Excipients may include, for example, nonionic solubilizers, such as cremophor, or proteins, such as human serum albumin or plasma preparations. If desired, the pharmaceutical composition to be administered may also contain non-toxic auxiliary substances, such as wetting or emulsifying agents, preservatives, and pH buffering agents and the like, for example, sodium acetate or sorbitan monolaurate.

The dosage form of the pharmaceutical composition will be determined by the mode of administration chosen. Embodiments of the disclosed pharmaceutical compositions may take a form suitable for virtually any mode of administration, including, for example, topical, ocular, oral, buccal, systemic, nasal, injection, transdermal, rectal, vaginal, etc., or a form suitable for administration by inhalation or insufflation.

Topical preparations may include eye drops, gels, ointments, creams, suspensions, sprays and the like as are well-known in the art.

Useful injectable preparations include sterile suspensions, solutions or emulsions of the active compound(s) in aqueous or oily vehicles. The compositions may also contain formulating agents, such as suspending, stabilizing and/or dispersing agent. The formulations for injection may be presented in unit dosage form, e.g., in ampules or in multidose containers, and may contain added preservatives.

Alternatively, the injectable formulation may be provided in powder form for reconstitution with a suitable vehicle, including but not limited to sterile pyrogen free water, buffer, dextrose solution, etc., before use. To this end, the active compound(s) maybe dried by any art-known technique, such as lyophilization, and reconstituted prior to use.

For transmucosal administration, penetrants appropriate to the barrier to be permeated are used in the formulation. Such penetrants are known in the art.

Systemic formulations include those designed for administration by injection, e.g., subcutaneous, intravenous, intramuscular, intrathecal or intraperitoneal injection, as well as those designed for transdermal, transmucosal, oral or pulmonary administration.

Oral formulations may be liquid (e.g., syrups, solutions or suspensions), or solid (e.g., powders, pills, tablets, or capsules). Solid compositions prepared by conventional means with pharmaceutically acceptable excipients such as binding agents (e.g., pregelatinised maize starch, polyvinylpyrrolidone or hydroxypropyl methylcellulose); fillers (e.g., lactose, mannitol, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). The tablets may be coated by methods well known in the art with, for example, sugars, films or enteric coatings. Actual methods of preparing such dosage forms are known, or will be apparent, to those skilled in the art.

Liquid preparations for oral administration may take the form of, for example, elixirs, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol, Cremophore™ or fractionated vegetable oils); and preservatives (e.g., methyl or propyl-p-hydroxybenzoates or sorbic acid). The preparations may also contain buffer salts, preservatives, flavoring, coloring and sweetening agents as appropriate. Preparations for oral administration may be suitably formulated to give controlled release of the active compound, as is well known.

For buccal administration, the compositions may take the form of tablets or lozenges formulated in conventional manner.

For rectal and vaginal routes of administration, the active compound(s) may be formulated as solutions (for retention enemas) suppositories or ointments containing conventional suppository bases such as cocoa butter or other glycerides.

For nasal administration or administration by inhalation or insufflation, the active compound(s) can be conveniently delivered in the form of an aerosol spray from pressurized packs or a nebulizer with the use of a suitable propellant, e.g., dichlorodifluoromethane, trichlorofluoromethane, dichlorotetrafluoroethane, fluorocarbons, carbon dioxide or other suitable gas. In the case of a pressurized aerosol, the dosage unit may be determined by providing a valve to deliver a metered amount. Capsules and cartridges for use in an inhaler or insufflator (for example capsules and cartridges comprised of gelatin) may be formulated containing a powder mix of the compound and a suitable powder base such as lactose or starch.

For ocular administration, the active compound(s) may be formulated as a solution, emulsion, suspension, etc. suitable for administration to the eye. A variety of vehicles suitable for administering compounds to the eye are known in the art. Specific non-limiting examples are described in U.S. Pat. Nos. 6,261,547; 6,197,934; 6,056,950; 5,800,807; 5,776,445; 5,698,219; 5,521,222; 5,403,841; 5,077,033; 4,882,150; and 4,738,851.

For prolonged delivery, the active compound(s) can be formulated as a depot preparation for administration by implantation or intramuscular injection. The active ingredient maybe formulated with suitable polymeric or hydrophobic materials (e.g., as an emulsion in an acceptable oil) or ion exchange resins, or as sparingly soluble derivatives, e.g., as a sparingly soluble salt. Alternatively, transdermal delivery systems manufactured as an adhesive disc or patch which slowly releases the active compound(s) for percutaneous absorption may be used. To this end, permeation enhancers may be used to facilitate transdermal penetration of the active compound(s). Suitable transdermal patches are described in for example, U.S. Pat. Nos. 5,407,713; 5,352,456; 5,332,213; 5,336,168; 5,290,561; 5,254,346; 5,164,189; 5,163,899; 5,088,977; 5,087,240; 5,008,110; and 4,921,475.

Alternatively, other pharmaceutical delivery systems may be employed. Liposomes and emulsions are well-known examples of delivery vehicles that may be used to deliver active compound(s) or prodrug(s). Certain organic solvents such as dimethylsulfoxide (DMSO) may also be employed, although usually at the cost of greater toxicity.

Certain embodiments of the pharmaceutical compositions comprising biologically active chrysophaentins as described herein may be formulated in unit dosage form suitable for individual administration of precise dosages. The pharmaceutical compositions may, if desired, be presented in a pack or dispenser device which may contain one or more unit dosage forms containing the active compound(s). The pack may, for example, comprise metal or plastic foil, such as a blister pack. The pack or dispenser device may be accompanied by instructions for administration. The amount of biologically active chrysophaentin administered will depend on the subject being treated, the severity of the affliction, and the manner of administration, and is known to those skilled in the art. Within these bounds, the formulation to be administered will contain a quantity of the compounds disclosed herein in an amount effective to achieve the desired effect in the subject being treated.

Embodiments of the disclosed chrysophaentin compounds will generally be used in an amount effective to achieve the intended result, for example in an amount effective to treat or prevent the particular disease being treated, such as a microbial or bacterial infection, for example, a Gram-positive, Gram-negative, or acid-fast bacterial infection. The compound(s) may be administered therapeutically to achieve therapeutic benefit or prophylactically to achieve prophylactic benefit. By therapeutic benefit is meant eradication or amelioration of the underlying disorder being treated and/or eradication or amelioration of one or more of the symptoms associated with the underlying disorder such that the patient reports an improvement in feeling or condition, notwithstanding that the patient may still be afflicted with the underlying disorder. Therapeutic benefit also includes halting or slowing the progression of the disease, regardless of whether improvement is realized.

For prophylactic administration, the chrysophaentin compound may be administered to a patient at risk of developing a disease caused by a bacterial pathogen. Compounds may also be administered prophylactically to healthy individuals who are repeatedly exposed to pathogenic bacteria known to produce disease or infection to prevent the onset of the disease or infection. For example, a compound may be administered to a healthy individual who is repeatedly exposed to drug-resistant bacteria.

The amount of compound administered will depend upon a variety of factors, including, for example, the particular indication being treated, the mode of administration, whether the desired benefit is prophylactic or therapeutic, the severity of the indication being treated and the age and weight of the patient, the bioavailability of the particular active compound, etc. Determination of an effective dosage is well within the capabilities of those skilled in the art.

Effective dosages may be estimated initially from in vitro assays. For example, an initial dosage may be formulated to achieve a circulating blood or serum concentration of active compound that is at or above an $IC_{50}$ of the particular compound as measured in an in vitro assay. Calculating dosages to achieve such circulating blood or serum concentrations taking into account the bioavailability of the particular compound is well within the capabilities of skilled artisans. For guidance, the reader is referred to Fingl & Woodbury, "General Principles," In: Goodman and Gilman's The Pharmaceutical Basis of Therapeutics, Chapter 1, pp. 1 46, latest edition, Pagamonon Press, and the references cited therein.

Initial dosages can also be estimated from in vivo data, such as animal models. Animal models useful for testing the efficacy of compounds to treat or prevent the various diseases described above are well-known in the art. Ordinarily skilled artisans can routinely adapt such information to determine dosages suitable for human administration.

Dosage amounts may be in the range of from about 0.0001 or 0.001 or 0.01 mg/kg/day to about 100 mg/kg/day, but may be higher or lower, depending upon, among other factors, the activity of the chrysophaentin compound, its bioavailability, the mode of administration and various factors discussed above. Dosage amount and interval may be adjusted individually to provide plasma levels of the compound(s) which are sufficient to maintain therapeutic or prophylactic effect. For example, the compounds may be administered once per week, several times per week (e.g., every other day), once per day or multiple times per day, depending upon, among other things, the mode of administration, the specific indication being treated and the judgment of the prescribing physician. In cases of local administration or selective uptake, such as local topical administration, the effective local concentration of active compound(s) may not be related to plasma concentration. Skilled artisans will be able to optimize effective local dosages without undue experimentation.

Preferably, the compound(s) will provide therapeutic or prophylactic benefit without causing substantial toxicity. Toxicity of the compound(s) may be determined using standard pharmaceutical procedures. The dose ratio between toxic and therapeutic (or prophylactic) effect is the therapeutic index. Compound (s) that exhibit high therapeutic indices are preferred.

Certain embodiments of the pharmaceutical methods and compositions include co-administration of the biologically active chrysophaentin compound(s) as described herein and a therapeutically effective amount of a second agent other than the chrysophaentin compound(s). The chrysophaentin and the second agent may be administered either separately or together in a single composition If a chrysophaentin compound is ineffective or insufficiently effective against a particular bacterium, the a second agent is used that enhances, or increases, the effectiveness of the chrysophaentin. In some embodiments, the second agent is an antimicrobial agent that increases the effectiveness of the pharmaceutical composition relative to a pharmaceutical composition comprising only a chrysophaentin compound as an active agent.

Bacteria are classified as Gram-negative or Gram-positive depending on whether they retain crystal violet dye in the Gram staining protocol. Other organisms such as *Mycobacteria, Nocardia*, and coccidian parasites are classified as acid-fast organisms using the Ziehl-Neelsen stain. All of these classes of organisms may be deleterious to humans. However, treating disorders, conditions or diseases caused by Gram-negative bacteria can be particularly challenging because Gram-negative bacteria have an outer lipopolysaccharide membrane that provides these bacteria with resistance to certain antibiotics that would normally target the cell wall or inner membrane. The outer membrane of the Gram-negative bacterium may inhibit penetration of the chrysophaentin compound through the outer membrane so that it can effectively inhibit FtsZ within the bacterial cell. In such instances, a second agent capable of increasing penetration of the chrysophaentin compound into the bacterium may be included in the pharmaceutical composition or may be administered substantially concurrently with the pharmaceutical composition so that the bacterium is exposed to both the chrysophaentin compound and the second agent.

Suitable second agents include antibiotic compounds, such as aminoglycosides, carbapenems, cephalosporins, glycopeptides, lincosamides, lipopeptides, macrolides, monobactams, nitrofurans, penicilllins, penicillin combinations, polypeptides, quinolones, sulfonamides, tetracyclines, anti-mycobacterial compounds, and others. Exemplary aminoglycosides include amikacin, gentamicin, kanamycin, neomycin, netilmicin, tobramycin, and paromycin. Exemplary carbapenems include ertapenem, doripenem, imipenem, cilastatin, and meropenem. Exemplary cephalosporins include cefadroxil, cefazolin, cefalotin, cephalexin, cefaclor, cefamandole, cefoxitin, cefprozil, cefuroxime, cefixime, cefdinir, cefditoren, cefoperazone, cefotaxime, cefpodoxime, ceftazidime, ceftibuten, ceftizoxime, ceftriaxone, cefepime, and cefobiprole. Exemplary glycopeptides include teicoplanin, vancomycin, and telavancin. Exemplary lincosamides include clindamycin and incomysin. Daptomycin is an exemplary lipopeptide. Exemplary macrolides include azithromycin, clarithromycin, dirithromycin, erythromycin, roxithromycin, troleandomycin, telithromycin, and spectinomycin. Aztreonam is an exemplary monobactam. Exemplary nitrofurans include furazolidone and nitrofurantoin. Exemplary penicillins include amoxicillin, ampicillin, azlocillin, carbenicillin, cloxacillin, dicloxacillin, flucloxacillin, mezlocillin, methicillin, nafcillin, oxacillin, penicillin G, penicillin, V, piperacillin, temocillin, and ticarcillin. Exemplary penicillin combinations include amoxicillin/clavulanate, ampicillin/sulbactam, piperacillin/tazobactam, and ticarcillin/clavulanate. Exemplary polypeptide antibiotics include bacitracin, colistin, and polymyxin B. Exemplary quinolones include ciprofloxacin, enoxacin, gatifloxacin, levofloxacin, lomefloxacin, moxifloxacin, nalidixic acid, norfloxacin, ofloxacin, trovafloxacin, grepafloxacin, sparfloxacin, and temafloxacin. Exemplary sulfonamides include mafenide, sulfonamidochrysoidine, sulfacetamide, sulfadiazine, silver sulfadiazine, sulfamethizole, sulfamethoxazole, sulfanilimide, sulfasalazine, sulfisoxazole, trimethoprim, and trimethoprim-sulfamethoxaxzole (cotrimoxazole). Exemplary tetracyclines include demeclocycline, doxycycline, minocycline, oxytetracycline, and tetracycline. Exemplary anti-mycobacterial antibiotics include clofazimine, dapsone, capreomycin, cycloserine, ethambutol, ethionamide, isoniazid, pyrazinamide, rifampicin (rifampin), rifabutin, rifapentine, and streptomycin. Other exemplary antibiotics include arsphenamine, chloramphenicol, fosfomycin, fusidic acid, linezolid, metronidazole, mupirocin, platensimycin, quinuprisin/dalfopristin, rifaximin, thiamphenicol, tigecycline, and timidazole.

In some embodiments, the second agent is a penetration enhancer selected to increase penetration of the chrysophaentin compound into the bacterium. For example, a combination of lysozyme with EDTA has been shown to be effective against the outer membrane of some Gram-negative organisms. Other drugs or compounds that may be useful in combination with a chrysophaentin compound against Gram-negative bacteria include carbapenems, some cephalosporins, and amine-containing cholic acid derivatives. Exemplary second agents that are effective against some Gram-negative bacteria include amoxicillin ampicillin, carbenicillin, cefaclor, cefepime, cefoxitin, cefpiromem cefprozil, cefuroxime, chloramphenicol, polymyxin B (for in vitro use), cefotaxime, streptomycin, and nalidixic acid.

XI. Therapeutic Uses

The present disclosure includes a treatment for disorders, conditions, or diseases resulting from microbial infection in a subject, such as infection with a bacterial pathogen. Gram-negative and Gram-positive bacteria, as well as acid-fast bacteria, may be pathogenic (i.e., disease causing) to humans, and can be treated with the chrysophaentin antibiotics. Bacterial species belonging to six Gram-positive genera are typically pathogenic in humans. These genera are *Streptococcus, Staphylococcus, Corynebacterium, Listeria, Bacillus*, and *Clostridium*. Other pathogenic Gram-positive bacteria include, but are not limited to, some *Mycobacterium* and *Enterococcus* species, e.g., *M. tuberculosis, M. leprae, E. faecalis* and *E. faecium*. The mycobacteria are classified as Gram-positive, acid-fast bacteria. Although they do not retain crystal violet stain, they are classified as Gram positive because they lack an outer cell membrane. Ziehl-Neesen acid-fast staining is therefore used to identify them.

Many species of Gram-negative bacteria are pathogenic, including but not limited to *Haemophilus influenza, Klebsiella pneumoniae, Legionella pneumophila, Pseudomonas aeruginosa, Escherichia coli, Proteus mirabilis, Enterobacter cloacae, Serratia marcescens, Helicobacter pylori, Salmonella enteritidis, Salmonella typhi, Acinetobacter baumannii, Neisseria gonorrhoeae, Neisseria meningitides*, and *Moraxella catarrhalis*. In some examples, the pathogen is a drug-susceptible bacteria, such as *Staphylococcus aureus, Enterococcus faecium*, or *Bacillus subtilis*, or a drug-resistant strain, such as methicillin-resistant *S. aureus* (MRSA), multidrug-resistant *S. aureus* (MDRSA) or vancomycin-resistant *E. faecium* (VREF).

The method of treating bacterial infections includes administering one or more chrysophaentin compounds of the present disclosure, or a combination of one or more chrysophaentin compounds along with one or more other pharmaceutical agents (also referred to herein as "drug" or "drugs"), to the subject in a pharmaceutically acceptable carrier and in an amount effective to treat a microbial infection, such as that caused by infection with a Gram-negative or Gram-positive bacterium (including infection with an acid-fast organism, such as *Mycobacteria*, for example *M. tuberculosis*). The one or more other pharmaceutical agents may be administered together with or separately from the one or more chrysophaentin compounds. The treatment can be used prophylactically in any subject in a demographic group at significant risk for such diseases; for example, patients who are at risk for infection with opportunistic bacterial pathogens (such as patients with AIDS or severe combined immunodeficiency, patients undergoing chemotherapy or radiation treatment, or transplant patients), or a patient in an environment (such as a nursing home or an in-patient hospital ward) that is known or suspected to harbor drug-resistant pathogens, such as MRSA. Alternatively, subjects can be selected using more specific criteria, such as a definitive diagnosis of a condition based on, for example, clinical signs and symptoms and/or laboratory evidence of bacterial infection. An example of such a subject would be a person in whom positive blood cultures have identified bacteremia with *Enterococcus faecium* (such as vancomycin-resistant *E. faecium*) or another organism that is known to be sensitive to inhibition with the chrysophaentin compounds. In some examples, the drug is administered to a subject from whom a bacteria has been obtained (such as by obtaining, e.g., a blood or sputum sample) and cultured, and the bacteria has been demonstrated in culture to be inhibited by (i.e., sensitive to) the chrysophaentin.

The vehicle in which the drug is delivered may include, e.g., the pharmaceutical compositions described above. Routes of administration include but are not limited to oral and parenteral routes, such as intravenous (iv), intraperitoneal (ip), rectal, topical, ophthalmic, nasal, and transdermal.

The drugs may be administered intravenously in any conventional medium for intravenous injection, such as an aqueous saline medium, or in blood plasma medium. The medium may also contain conventional pharmaceutical adjunct materials such as, for example, pharmaceutically acceptable salts to adjust the osmotic pressure, lipid carriers such as cyclodextrins, proteins such as serum albumin, hydrophilic agents such as methyl cellulose, detergents, buffers, preservatives and the like. A more complete explanation of parenteral pharmaceutical carriers can be found in *Remington: The Science and Practice of Pharmacy*, 19th Edition, Chapter 95, 1995.

Therapeutically effective doses of the chrysophaentin compounds and/or chrysophaentin analogues of the present disclosure can be determined by one of skill in the art, with a goal of achieving tissue concentrations that are at least as high as the $IC_{50}$ of the applicable chrysophaentin compound and/or chrysophaentin analogues disclosed in the examples herein.

XII. Examples

General Experimental. Optical rotations were measured with a Jasco P-2000 polarimeter, IR spectra were recorded on a Perkin Elmer FT-IR Spectrum One spectrometer, and UV spectra were recorded on an Agilent 8453 spectrophotometer. The accurate mass electrospray ionization (ESI) mass spectra were measured on a Waters LCT Premier time-of-flight (TOF) mass spectrometer. The instrument was operated in ω-mode at a nominal resolution of 10,000, and all data was recorded in the negative ion mode. The electrospray capillary voltage was set at 2 KV and the sample cone voltage at 30 V. The desolvation temperature was set to 275° C., and nitrogen was used as the desolvation gas with a flow rate of 300 L/h. Accurate masses were obtained using the internal reference standard method. In-source fragmentation was induced by increasing the cone voltage to 125 V.

NMR Spectroscopy. All NMR spectra were recorded on Bruker Avance spectrometers at 300 K. NMR spectra of natural products were recorded in $CD_3OD$ or $DMF-d_7$ at 600 MHz with an x,y,z-shielded gradient triple resonance probe, or at 500 MHz with a cryogenically cooled z-shielded gradient triple resonance probe. Samples were prepared in Shigemi NMR tubes with solvent-matched plungers. All spectra were referenced to residual solvent peaks corresponding to the deuterated solvents listed for each compound in their respective Tables. DQF-COSY, 2D-HOHAHA, HSQC, HMBC, and ROESY experiments were recorded using standard pulse programs with water suppression (Watergate). HSQC experiments were recorded with dwell times of 1.724 ms ($^1J_{C-H}$ 145 Hz), and HMBC spectra with dwell times of 31.25 and 50 ms ($^{2,3}J_{C-H}$=8 and 5 Hz). Long-range $^1H$-$^{13}C$ connectivities were assigned from HMBC spectra, and NOEs assigned from ROESY spectra. Correlations for each proton are included in the following tables.

Saturation transfer difference (STD) NMR experiments were recorded with the carrier set at −1 or 12 ppm for on-resonance irradiation and at 40 ppm for off-resonance irradiation. Control spectra were recorded under identical conditions on samples containing free compound 1 to test for artifacts. Selective protein saturation (2 s) was accomplished by using a train of 50 ms Gauss-shaped pulses, each separated by a 1 ms delay, at an experimentally determined optimal power (49 dB on our probe); a $T_{1\rho}$ filter (30 ms) was incorporated to suppress protein resonances. Experiments were recorded using a minimum of 1024 scans and 32K points. Onand off-resonance spectra were processed independently, and subtracted to provide a difference spectrum.

Computational Details. To allow full exploration of the conformational space of chrysophaentin 1, molecular dynamics (MD) calculations were performed at three different temperatures (300 K, 500 K, 700 K/50 ns) using the AMBER force field (MacroModel software package (Mohamadi et al., *J. Comput. Chem.*, 11:440, 1990)) to give 100 structures, each of which was minimized using the Polak-Ribier Conjugate Gradient algorithm (PRCG, 1000 steps, maximum derivative less than 0.05 kcal/mol). These calculations provided the lowest energy minimum conformer for chrysophaentin 1. A parallel analysis was performed using the MonteCarlo Multiple Minimum (MCMM) method (50K steps) of the MacroModel package, leading to the same results obtained by MD calculations. Docking of the lowest energy structure of compound 1 to an *E. coli* homology model of FtsZ (built using SWISS-MODEL (Arnold et al., Bioinformatics, 22:195, 2006) routines starting from the coordinates of *P. aeruginosa* FtsZ, pdb accession code 1ofu.pdb (Cordell et al., *Proc. Natl. Acad. Sci. U.S.A.*, 101:11821, 2003)) was carried out with the program Autodock Vina 1.0.3. After initial docking runs showed all reasonable models to place compound 1 in or near to the GTP binding site, the grid was narrowed to an area slightly larger than the GTP binding site (28×20×24 Å). Docking was carried out with an exhaustiveness value of 512 and a maximum output of 25 structures. Agreement with the STD NMR data and calculated energies was used to arrive at the best docked-model. This approach provided a model that displayed the fourth lowest energy of the group, and its position within the GTP binding site was in full agreement with the measured STD NMR enhancements.

Additional supporting information is available free of charge via the Internet at the ACS Publications website (Plaza et al., *J. Am. Chem. Soc.*, 132(26):9069-9077, 2010), and includes $^1$H NMR and $^{13}$C NMR data and spectra for compounds 1a, 2-4, 6-8; $^1$H NMR and STD NMR spectra for complex of 1/FtsZ in aqueous buffer; tubulin polymerization curves; and coordinates for the docked model of the global minimum energy structure of compound 1 to a homology model of *E. coli* FtsZ (pdb).

Example 1

Isolation and Structural Determination of Compounds

Samples of the chrysophyte alga *Chrysophaeum taylori* Lewis and Bryan (*Am. J. Bot.*, 28:343, 1941) were collected at −20 ft from Round Bay on the Island of St. John. The alga, found growing as fluffy colonies on coarse sand or coral rubble substrate, appears sulfur yellow in color, and when disturbed can turn to a rusty brown color within seconds. The multicellular structure of *C. taylori* is extremely fragile and the mucilaginous cells do not preserve well. However, when freshly collected or freshly preserved (2.5% glutaraldehyde in seawater) samples are viewed by light microscopy, stalk-like structure made up of branching mucilaginous 'streamers' of pear-shaped, invaginated cells were visible. In addition, algal collections contained the known styrylchromone hormothamnione, and bore a significant resemblance at all stages of handling to field notes published by Gerwick (*J. Nat. Prod.*, 52:252, 1989).

The antimicrobial compounds were isolated from samples of lyophilized *Chrysophaeum taylori* algae (200 g dry weight) by sequentially extracting with hexanes, chloroform, and methanol. The methanol extract (13 g) was partitioned between n-butanol-H$_2$O (1:1) and the organic layer (1.1 g) was fractionated on Sephadex LH-20. Fractions containing diarylalkene ethers (75.1 mg) were chromatographed by reverse-phase HPLC (2.5 mL/min) using a Jupiter Proteo C12 column (250×10 mm, 4µ particle size) with diode array UV detection at 220 and 280 nm. Compounds were eluted with a linear gradient of 50-80% MeOH in 0.05% TFA in 50 minutes to produce compounds 1 (3.5 mg, $t_R$=28.0 min), 2 (0.4 mg, $t_R$=28.6 min), 3 (0.8 mg, $t_R$=29.4 min), 4 (1.8 mg, $t_R$=32.0 min), 5 (2.6 mg, $t_R$=33.3 min), 6 (1.5 mg, $t_R$=41.3 min), 7 (1.4 mg, $t_R$=41.8 min), and 8 (0.7 mg, $t_R$=50.5 min).

Molecular formulae were obtained by high-resolution mass spectrometry and NMR:

Compound 1: colorless amorphous powder; nonoptically active; UV (MeOH) $\lambda_{max}$ (log ε) 210 (4.2), 225 (3.9), 290 (3.4); IR (film) $v_{max}$ 3384, 1675, 1449, 1203, 1143, 846, 802, 727; $^1$H and $^{13}$C NMR data, see Table 1; HR-ESI-MS 675.0154 [M-H]$^-$ corresponding to a molecular formula of $C_{32}H_{24}Cl_4O_8$ (calculated for $C_{32}H_{23}Cl_4O_8$, 675.0147).

Compound 2: colorless amorphous powder; nonoptically active; UV (MeOH) $\lambda_{max}$ (log ε) 210 (4.2), 225 (3.8), 290 (3.4); IR (film) $v_{max}$ 3381, 1681, 1608, 1447, 1207, 1143, 846, 802, 723; $^1$H and $^{13}$C NMR data, see Table 3; HR-ESI-MS 718.9655 [M-H]$^-$ corresponding to a molecular formula of $C_{32}H_{24}BrCl_3O_8$ (calculated for $C_{32}H_{23}BrCl_3O_8$, 718.9642).

Compound 3: colorless amorphous powder; nonoptically active; UV (MeOH) $\lambda_{max}$ (log ε) 210 (4.2), 225 (3.9), 290 (3.4); IR (film) $v_{max}$ 3387, 1680, 1608, 1444, 1209, 1145, 846, 802, 722; $^1$H and $^{13}$C NMR data, see Table 3; HR-ESI-MS 718.9650 [M-H]$^-$ corresponding to a molecular formula of $C_{32}H_{24}BrCl_3O_8$ (calculated for $C_{32}H_{23}BrCl_3O_8$, 718.9642).

Compound 4: colorless amorphous powder; nonoptically active; UV (MeOH) $\lambda_{max}$ (log ε) 210 (4.1), 225 (3.9), 290 (3.4); IR (film) $v_{max}$ 3397, 1681, 1608, 1447, 1207, 1144, 1016, 844, 802, 723; $^1$H and $^{13}$C NMR data, see Table 3; HR-ESI-MS 762.9168 [M-H]$^-$ corresponding to a molecular formula of $C_{32}H_{24}Br_2Cl_2O_8$ (calculated for $C_{32}H_{23}Br_2Cl_2O_8$, 762.9137).

Compound 5: colorless amorphous powder; nonoptically active; UV (MeOH) $\lambda_{max}$ (log ε) 210 (4.2), 225 (3.8), 290 (3.4); IR (film) $v_{max}$ 3386, 1686, 1608, 1451, 1201, 1148, 849, 808, 730; $^1$H and $^{13}$C NMR data, see Table 4; HR-ESI-MS 677.0317 [M-H]$^-$ corresponding to a molecular formula of $C_{32}H_{26}Cl_4O_8$ (calculated for $C_{32}H_{25}Cl_4O_8$, 677.00304).

Compound 6: colorless amorphous powder; nonoptically active; UV (MeOH) $\lambda_{max}$ (log ε) 210 (4.2), 225 (3.8), 290 (3.4); IR (film) $v_{max}$ 3385, 1675, 1606, 1453, 1201, 1144, 846, 802, 733; $^1$H and $^{13}$C NMR data, see Table 5; HR-ESI-MS 675.0140 [M-H]$^-$ corresponding to a molecular formula of $C_{32}H_{24}Cl_4O_8$ (calculated for $C_{32}H_{23}Cl_4O_8$, 675.0147).

Compound 7: colorless amorphous powder; nonoptically active; UV (MeOH) $\lambda_{max}$ (log ε) 210 (4.2), 225 (3.8), 290 (3.4); IR (film) $v_{max}$ 3381, 1677, 1601, 1435, 1210, 1148, 842, 812, 721; $^1$H and $^{13}$C NMR data, see Table 6; HR-ESI-MS 718.9620 [M-H]$^-$ corresponding to a molecular formula of $C_{32}H_{24}BrCl_3O_8$ (calculated for $C_{32}H_{23}BrCl_3O_8$, 718.9642).

Compound 8: colorless amorphous powder; nonoptically active; UV (MeOH) $\lambda_{max}$ (log ε) 210 (4.2), 225 (3.8), 290 (3.4); IR (film) $v_{max}$ 3381, 1678, 1605, 1447, 1207, 1144, 840, 802, 725; $^1$H and $^{13}$C NMR data, see Table 6; HR-ESI-MS 752.9255 [M-H]$^-$ corresponding to a molecular formula of $C_{32}H_{23}BrCl_4O_8$ (calculated for $C_{32}H_{22}BrCl_4O_8$, 752.9252).

TABLE 1

NMR Spectroscopic Data for Chrysophaentin 1

| position | 1 (MeOH-d$_4$) $\delta_C{}^a$ | $\delta_H{}^b$ (J in Hz) | HMBC$^c$ | ROESY$^d$ | 1 (DMF-d$_7$) $\delta_C{}^e$ | $\delta_H{}^f$ (J in Hz) | HMBC$^c$ | ROESY$^d$ |
|---|---|---|---|---|---|---|---|---|
| 1 | 148.1 | | | | 146.8 | | | |
| 2 | 120.0 | | | | 118.2 | | | |
| 3 | 117.1 | 6.81 s | 1, 2, 4, 5 | | 116.1 | 7.00 s | 1, 2, 4, 5 | OH-4 |
| 4 | 150.4 | | | | 149.7 | | | |
| OH-4 | | | | | | 9.90 s | 3, 4, 5 | 3, 8 |
| 5 | 126.7 | | | | 125.6 | | | |
| 6 | 116.0 | 6.179 s | 1, 2, 4, 5, 7 | | 115.2 | 6.39 s | 1, 2, 4, 5 | 7, 10, OH-15' |
| 7 | 30.6 | 3.23 d (8.7) | 4, 5, 6, 8, 9 | 10 | 29.8 | 3.36 d (8.8) | 4, 5, 8, 9 | 6, 8, 10 |
| 8 | 127.7 | 5.99 t (8.7) | 5, 7, 9, 10 | | 126.3 | 6.05 t (8.8) | 7, 9, 10 | 7 |
| 9 | 134.7 | | | | 134.4 | | | |
| 10 | 33.7 | 3.39 br s | 8, 9, 11, 12, 16 | 7, 12, 6' | 32.3 | 3.57 | 8, 9, 11, 12 | 6, 7, 6' |
| 11 | 133.0 | | | | 131.7 | | | |
| 12 | 107.9 | 6.18 d (2.8) | 10, 13, 14, 16 | 10 | 106.7 | 6.27 d (2.6) | 13, 14, 15, 16 | 10, OH-13 |
| 13 | 155.6 | | | | 155.5 | | | |
| OH-13 | | | | | | 9.41 s | 12, 13, 14 | 12, 14 |
| 14 | 103.8 | 6.30 d (2.8) | 12, 13, 15, 16 | | 103.1 | 6.48 d (2.8) | 12, 16, 13, 15 | OH-14, OH-13 |
| 15 | 151.3 | | | | 150.7 | | | |
| OH-15 | | | | | | 9.58 s | 14, 15, 16 | 14 |
| 16 | 135.9 | | | | 134.9 | | | |
| 1' | 148.9 | | | | 147.9 | | | |
| 2' | 121.1 | | | | 120.1 | | | |
| 3' | 117.3 | 6.84 s | 1', 2', 4', 5' | | 116.0 | 7.05 s | 1', 2', 4', 5' | OH-4' |
| 4' | 150.7 | | | | 150.4 | | | |
| OH-4' | | | | | | 10.1 s | 3', 4', 5' | 3', 8' |
| 5' | 127.2 | | | | 125.9 | | | |
| 6' | 116.7 | 6.28 s | 1', 2', 4', 5', 7' | 8', 10', 10 | 116.4 | 6.51 s | 1', 2', 4', 5', 7' | |
| 7' | 30.4 | 3.28 br d (8.1) | 4', 5', 6', 9' | 10 | 30.3 | 3.36 br d (8.3) | 8' | 6', 8' |
| 8' | 127.7 | 6.07 t (8.1) | 5', 7', 9', 10' | 6', 10' | 127.1 | 6.23 t (8.3) | 9' | 7' |
| 9' | 134.4 | | | | 133.1 | | | |
| 10' | 40.6 | 3.57 br s | 8', 9', 11', 12' | 6', 7', 8', 12' | 39.2 | 3.72 | | |
| 11' | 136.7 | | | | 135.7 | | | |
| 12', 16' | 109.1 | 6.16 br s | 12', 13', 14' | 10' | 107.6 | 6.25 | 11' | OH-13' |
| 13', 15' | 151.8 | | | | 151.2 | | | |
| OH-13', OH-15' | | | | | | 9.44 s | 13', 14' | 6, 12' |
| 14' | 129.7 | | | | 128.6 | | | |

$^a$Recorded at 125 MHz; referenced to residual MeOH-d$_4$ at δ 49.1.
$^b$Recorded at 500 MHz; referenced to residual MeOH-d$_4$ at δ 3.30.
$^c$Proton showing HMBC correlation to indicated carbon.
$^d$Proton showing ROESY correlation to indicated carbon.
$^e$Recorded at 125 MHz; referenced to residual DMF-d$_7$ at δ 34.89.
$^f$Recorded at 500 MHz; referenced to residual DMF-d$_7$ at δ 2.92.

TABLE 2

$^1$H and $^{13}$C NMR Data for Compound 1a (MeOH-d$_4$).

| position | $\delta_C{}^a$ | $\delta_H{}^b$ (J in Hz) |
|---|---|---|
| 1 | 151.9 | |
| 2 | 120.6 | |
| 3 | 125.1 | 7.21 s |
| 4 | 145.5 | |
| OAc-4 | 20.7 | 2.32 s |
| 5 | 132.5 | |
| 6 | 117.6 | 6.48 s |
| 7 | 28.8 | 3.28$^c$ |
| 8 | 127.4 | 5.92 t (8.2) |
| 9 | 135.3 | |
| 10 | 33.4 | 3.71, 3.45 br s |
| 11 | 133.8 | |
| 12 | 121.3 | 6.95$^c$ |
| 13 | 148.6 | |
| OAc-13 | 20.7 | 2.27 |
| 14 | 118.1 | 6.96$^c$ |
| 15 | 143.7 | |
| OAc-15 | 20.2 | 1.91 |
| 16 | 143.7 | |
| 1' | 152.6 | |
| 2' | 122.0 | |
| 3' | 125.8 | 7.34 s |
| 4' | 145.1 | |
| OAc-4' | 20.6 | 2.37 |
| 5' | 134.4 | |
| 6' | 117.7 | 6.50 s |
| 7' | 29.1 | 3.28$^c$) |
| 8' | 127.5 | 6.04 t (8.4) |
| 9' | 136.4 | |
| 10' | 39.9 | 3.63 br s |
| 11' | 136.7 | |
| 12', 16' | N.O. | N.O. |
| 13', 15' | N.O. | |
| OAc-13', OAc-15' | 20.1 | 2.04 br s |
| 14' | N.O. | |

$^a$Recorded at 125 MHz; referenced to residual CD$_3$OD at δ 49.15 ppm.
$^b$Recorded at 500 MHz; referenced to residual CD$_3$OD at δ 3.31 ppm.

TABLE 3

$^1$H and $^{13}$C NMR Data for Compounds 2-4 (MeOH-d$_4$).

| | 2 | | 3 | | 4 | |
|---|---|---|---|---|---|---|
| Position | $\delta_C{}^a$ | $\delta_H{}^b$ (J in Hz) | $\delta_C{}^a$ | $\delta_H{}^b$ (J in Hz) | $\delta_C{}^a$ | $\delta_H{}^b$ (J in Hz) |
| 1 | 148.0 | | 149.2 | | 149.0 | |
| 2 | 120.0 | | 108.2 | | 108.1 | |
| 3 | 117.1 | 6.81 s | 119.7 | 6.99 s | 119.9 | 6.97 s |
| 4 | 150.3 | | 150.6 | | 150.5 | |
| 5 | 126.8 | | 127.3 | | 127.2 | |
| 6 | 115.9 | 6.17 s | 115.9 | 6.16 s | 115.9 | 6.16 s |
| 7 | 30.6 | 3.22 d (8.7) | 30.7 | 3.22 d (8.7) | 30.6 | 3.22 d (8.7) |
| 8 | 127.6 | 5.99 t (8.7) | 127.5 | 5.99 t (8.7) | 127.5 | 6.00 t (8.7) |
| 9 | 134.4 | | 134.4 | | 134.4 | |
| 10 | 33.5 | 3.39 br s | 33.6 | 3.39 br s | 33.6 | 3.39 br s |
| 11 | 133.0 | | 133.0 | | 132.8 | |
| 12 | 107.8 | 6.18 d (2.8) | 107.7 | 6.18 d (2.8) | 107.9 | 6.17 d (2.8) |
| 13 | 155.6 | | 155.6 | | 155.4 | |
| 14 | 103.8 | 6.30 d (2.8) | 103.8 | 6.30 d (2.8) | 103.7 | 6.30 d (2.8) |
| 15 | 151.3 | | 151.2 | | 151.1 | |
| 16 | 135.9 | | 135.8 | | 135.7 | |
| 1' | 149.5 | | 148.7 | | 149.5 | |
| 2' | 109.3 | | 121.0 | | 109.3 | |
| 3' | 120.0 | 7.00 s | 117.2 | 6.84 s | 119.9 | 7.00 s |
| 4' | 150.8 | | 150.6 | | 150.8 | |
| 5' | 127.6 | | 127.1 | | 127.7 | |
| 6' | 116.3 | 6.25 s | 116.4 | 6.27 s | 116.2 | 6.25 s |
| 7' | 30.4 | 3.28 br d (8.1) | 30.4 | 3.28 br d (8.1) | 30.4 | 3.28 br d (8.1) |
| 8' | 127.6 | 6.06 t (8.1) | 127.6 | 6.06 t (8.1) | 127.7 | 6.05 t (8.1) |
| 9' | 134.2 | | 134.2 | | 134.1 | |
| 10' | 40.5 | 3.57 br s | 40.5 | 3.57 br s | 40.4 | 3.57 br s |
| 11' | 136.7 | | 136.3 | | 136.3 | |
| 12', 16' | 108.9 | 6.16 br s | 108.8 | 6.16 br s | 108.9 | 6.16 br s |
| 13', 15' | 151.8 | | 151.8 | | 151.6 | |
| 14' | 129.7 | | 129.7 | | 129.7 | |

$^a$Recorded at 125 MHz; referenced to residual MeOH-d$_4$ at $\delta$ 49.1.
$^b$Recorded at 500 MHz; referenced to residual MeOH-d$_4$ at $\delta$ 3.30.

TABLE 4

NMR Spectroscopic Data for Chrysophaentin 5

| | 5 (MeOH-d$_4$) | | | 5 (DMF-d$_7$) | | | |
|---|---|---|---|---|---|---|---|
| position | $\delta_C{}^a$ | $\delta_H{}^b$ (J in Hz) | HMBC$^c$ | $\delta_C{}^e$ | $\delta_H{}^f$ (J in Hz) | HMBC$^c$ | ROESY$^d$ |
| 1 | 148.3 | | | 147.3 | | | |
| 2 | 120.6 | | | 119.4 | | | |
| 3 | 116.9 | 6.84 s | 1, 2, 4, 5 | 116.3 | 7.01 s | 1, 2, 4, 5 | OH-4 |
| 4 | 150.6 | | | 150.2 | | | |
| OH-4 | | | | | 9.82 s | 3, 4, 5 | 3 |
| 5 | 126.5 | | | 125.6 | | | |
| 6 | 116.5 | 6.44 s | 1, 2, 4, 5, 7 | 115.8 | 6.58 s | 1, 2, 4, 5, 7 | 7 |
| 7 | 30.0 | 3.32 d (7.9) | 4, 5, 6, 8, 9 | 29.3 | 3.41 d (7.5) | 1, 4, 5, 8, 9 | 6, 8, 10 |
| 8 | 127.6 | 5.73 t (7.9) | 5, 7, 9, 10 | 127.3 | 5.74 t (7.5) | 5, 7, 9, 10 | 7 |
| 9 | 134.2 | | | 133.2 | | | |
| 10 | 40.5 | 3.52 br s | 8, 9, 11, 12 | 39.7 | 3.61 br s | 8, 9, 11, 12 | 7, 12 |
| 11 | 140.9 | | | 139.8 | | | |
| 12, 16 | 108.1 | 6.16 br d (1.9) | 10, 13, 14, 16 | 107.2 | 6.25 br s | 10, 13, 14, 16 | OH-13 |
| 13, 15 | 159.3 | | | 159.3 | | | |
| OH-13, OH-15 | | | | | 9.34 s | 12, 13, 14 | 12, 14 |
| 14 | 101.6 | 6.13 br d (1.9) | 12, 13 | 101.2 | 6.26 d (1.8) | 12, 13 | OH-13 |
| 1' | 146.8 | | | 146.6 | | | |
| OH-1' | | | | | 9.52 s | 1', 2', 6' | 6' |
| 2' | 119.1 | | | 120.3 | | | |
| 3' | 116.8 | 6.74 s | 1', 2', 4', 5' | 115.9 | 6.91 s | 1', 2', 5' | OH-4' |
| 4' | 149.4 | | | 148.8 | | | |
| OH-4' | | | | | 9.55 s | 3', 4', 5' | 3' |
| 5' | 127.1 | | | 126.1 | | | |
| 6' | 118.4 | 6.70 s | 1', 2', 4', 5', 7' | 117.8 | 6.90 s | 2', 4', 7' | OH-1', 7', 8' |
| 7' | 29.9 | 3.41 d (7.9) | 4', 5', 6', 8', 9' | 29.0 | 3.48 | 5', 6', 8', 9' | 6', 8', 10' |
| 8' | 128.3 | 5.88 t (7.9) | 5', 7', 9', 10' | 127.5 | 5.92 t (7.7) | 5', 9', 10' | 6', 7' |
| 9' | 133.4 | | | 133.1 | | | |
| 10' | 40.3 | 3.69 br s | 8', 9', 11', 12' | 39.3 | 3.74 br s | 8', 9', 11', 12' | 7', 12' |
| 11' | 136.4 | | | 135.1 | | | |
| 12', 16' | 109.3 | 6.41 s | 10', 12', 13', 14' | 108.3 | 6.49 | 11', 12', 13', 14' | 10', OH-13' |
| 13', 15' | 151.6 | | | 151.5 | | | |
| OH-13', OH-15' | | | | | 9.60 s | 12', 13', 14' | 12' |
| 14' | 130.3 | | | 129.4 | | | |

$^a$Recorded at 125 MHz; referenced to residual MeOH-d$_4$ at $\delta$ 49.1.
$^b$Recorded at 500 MHz; referenced to residual MeOH-d$_4$ at $\delta$ 3.30.
$^c$Proton showing HMBC correlation to indicated carbon.
$^d$Proton showing ROESY correlation to indicated carbon.
$^e$Recorded at 125 MHz; referenced to residual DMF-d$_7$ at $\delta$ 34.89.
$^f$Recorded at 500 MHz; referenced to residual DMF-d$_7$ at $\delta$ 2.92.

TABLE 5

Spectroscopic NMR Data for Compound 6 in MeOH-d$_4$ and DMF-d$_7$

| Position | 6 (MeOH-d$_4$) | | | | 6 (DMF-d$_7$) | | |
|---|---|---|---|---|---|---|---|
| | $\delta_C{}^a$ | $\delta_H{}^b$ (J in Hz) | HMBC$^c$ | ROESY$^d$ | $\delta_C{}^e$ | $\delta_H{}^f$ (J in Hz) | HMBC$^c$ |
| 1', 1' | 148.2 | | | | 147.0 | | |
| 2, 2' | 120.4 | | | | 119.0 | | |
| 3, 3' | 117.3 | 6.90 s | 1, 2, 4, 5, 6, 7 | | 116.4 | 7.06 s | 1, 2, 4, 5 |
| 4, 4' | 150.7 | | | | 150.1 | | |
| OH-4, OH-4' | | | | | | 9.98 s | 3, 4, 5 |
| 5, 5' | 126.5 | | | | 125.9 | | |
| 6, 6' | 115.1 | 6.42 s | 1, 2, 3, 4, 5, 7 | 7, 8, 12 | 114.3 | 6.55 | 1, 2, 4, 7 |
| 7, 7' | 31.0 | 3.35 d (8.3) | 4, 5, 6, 8, 9 | 10 | 30.3 | 3.43 d (8.5) | 4, 5, 8, 9 |
| 8, 8' | 127.2 | 5.89 t (8.3) | 5, 7, 9, 10, 11 | 7 | 126.7 | 6.00 t (8.5) | 9 |
| 9, 9' | 134.3 | | | | 133.2 | | |
| 10, 10' | 39.8 | 3.54 br s | 8, 9, 11, 12, 16 | 7, 12 | 38.9 | 3.65 br s | 8, 9, 11, 12 |
| 11, 11' | 137.0 | | | | 135.9 | | |
| 12, 16, 12', 16' | 110.0 | 6.23 s | 9, 10, 11, 12, 13, 14, 15, 16 | 6, 10 | 108.6 | 6.34 s | 10, 11, 12, 13, 14 |
| 13, 15, 13', 15' | 151.3 | | | | 151.1 | | |
| OH-13, OH-15 OH-13', OH-15' | | | | | | 9.79 | NO |
| 14, 14' | 130.0 | | | | 128.8 | | |

$^a$Recorded at 125 MHz; referenced to residual MeOH-d$_4$ at δ 49.1.
$^b$Recorded at 500 MHz; referenced to residual MeOH-d$_4$ at δ 3.30.
$^c$Proton showing HMBC correlation to indicated carbon.
$^d$Proton showing ROESY correlation to indicated carbon.
$^e$Recorded at 125 MHz; referenced to residual DMF-d$_7$ at δ 34.89.
$^f$Recorded at 500 MHz; referenced to residual DMF-d$_7$ at δ 2.92.

TABLE 6

$^1$H and $^{13}$C NMR Data for Compounds 7 and 8 (MeOH-d$_4$)

| Position | 7 | | 8 | |
|---|---|---|---|---|
| | $\delta_C{}^a$ | $\delta_H{}^b$ (J in Hz) | $\delta_C{}^a$ | $\delta_H{}^b$ (J in Hz) |
| 1 | 148.1 | | 147.7 | |
| 2 | 120.3 | | 120.5 | |
| 3 | 117.3 | 6.90 s | 117.3 | 6.91 s |
| 4 | 150.7 | | 151.0 | |
| 5 | 126.6 | | 126.8 | |
| 6 | 115.1 | 6.42 s | 115.1 | 6.41 s |
| 7 | 31.1 | 3.35 d (8.0) | 30.9 | 3.35 d (8.1) |
| 8 | 127.2 | 5.89 t (8.0) | 126.8 | 5.97 t (8.1) |
| 9 | 134.3 | | 134.4 | |
| 10 | 39.6 | 3.54 s | 39.9 | 3.53 br s |
| 11 | 137.0 | | 137.1 | |
| 12, 16 | 110.1 | 6.22 s | 130.1 | 6.21 s |
| 13, 15 | 151.8 | | 151.1 | |
| 14 | 130.2 | | 130.0 | |
| 1' | 149.3 | | 148.1 | |
| 2' | 108.9 | | 120.3 | |
| 3' | 120.3 | 7.06 s | 117.3 | 6.90 s |
| 4' | 151.0 | | 150.7 | |
| 5' | 127.3 | | 126.5 | |
| 6' | 115.1 | 6.41 s | 115.1 | 6.40 s |
| 7' | 31.1 | 3.34 d (8.0) | 30.6 | 3.35 d (8.2) |
| 8' | 127.2 | 5.89 t (8.0) | 127.8 | 5.89 t (8.2) |
| 9' | 134.3 | | 133.5 | |
| 10' | 39.6 | 3.54 s | 38.6 | 3.89 br s |
| 11' | 137.0 | | 135.8 | |
| 12' | 110.05 | 6.23 s | 106.3 | |
| 13' | 151.2 | | 146.1 | |
| 14' | 130.0 | | 130.7 | |
| 15' | 151.2 | | 150.0 | |
| 16' | 110.0 | 6.23 | 109.1 | 6.22 s |

$^a$Recorded at 125 MHz; referenced to residual MeOH-d$_4$ at δ 49.1.
$^b$Recorded at 500 MHz; referenced to residual MeOH-d$_4$ at δ 3.30.

Example 2

Antimicrobial Testing of Compounds 1, 1a, 4-8

Compounds 1-8 were tested for antimicrobial activity against *Staphylococcus aureus* (SA, ATCC 25923), methicillin-resistant *S. aureus* (MRSA, ATCC BAA-41), multidrug-resistant *S. aureus* (MDRSA, ATCC BAA-44), *Enterococcus faecium* (EF, ATCC 49032), vancomycin-resistant *E. Faecium* (VRE, ATCC 700221), and *Bacillus subtilis* (ATCC 49343) using a modified disk diffusion assay and microbroth liquid dilution assays. For disk diffusion assays, agar plates seeded with suspensions of bacteria were prepared by adding 500 µL of a 24 h culture of bacteria to 100 mL of autoclaved Mueller Hinton II agar and cooled to 55° C. Seeded liquid agar (10 mL) was transferred immediately to square Petri dishes and allowed to cool for 1 h. Control drugs used for each microorganism included kanamycin (50 µg) for *S. aureus*, and nitrofurantoin (25 µg) for MRSA. Following incubation at 37° C. for 18 h, zones of inhibition were measured. MIC$_{so}$ values for compounds 1 and 4-8 were determined using a microbroth dilution assay outlined in the Clinical and Laboratory Standards Institute methods for susceptibility tests for bacteria that grow aerobically. Briefly, single bacterial colonies were used to inoculate 4 mL of Trypticase Soy broth (BD) for overnight growth and inoculum for each were diluted to 5×10$^5$ CFU/mL using the 0.5 McFarland standard. In a 96 well plate (Costar, round bottom), control antibiotics (oxacillin for SA and MRSA, vancomycin for EF and VRE, chloramphenicol for *B. subtilis*) or natural product inhibitors were added to Muller Hinton II broth (for *S. aureus*, MRSA, and *B. subtilis*) or 10% brain heart infusion broth (for *E. faecium* and VRE) in the first column of the well plates, and serially diluted across the plate, reserving wells for a positive growth control (no treatment). 10 µL of diluted bacteria were added to all wells with the exception of those kept for broth blanks (MHII or brain heart infusion broth only). Plates were incubated at 37° C. overnight and read at absorbance 600 nm on a Molecular Devices plate reader. Growth curves were plotted and $IC_{50}$ values obtained using Kalidagraph software.

Figure 7A:
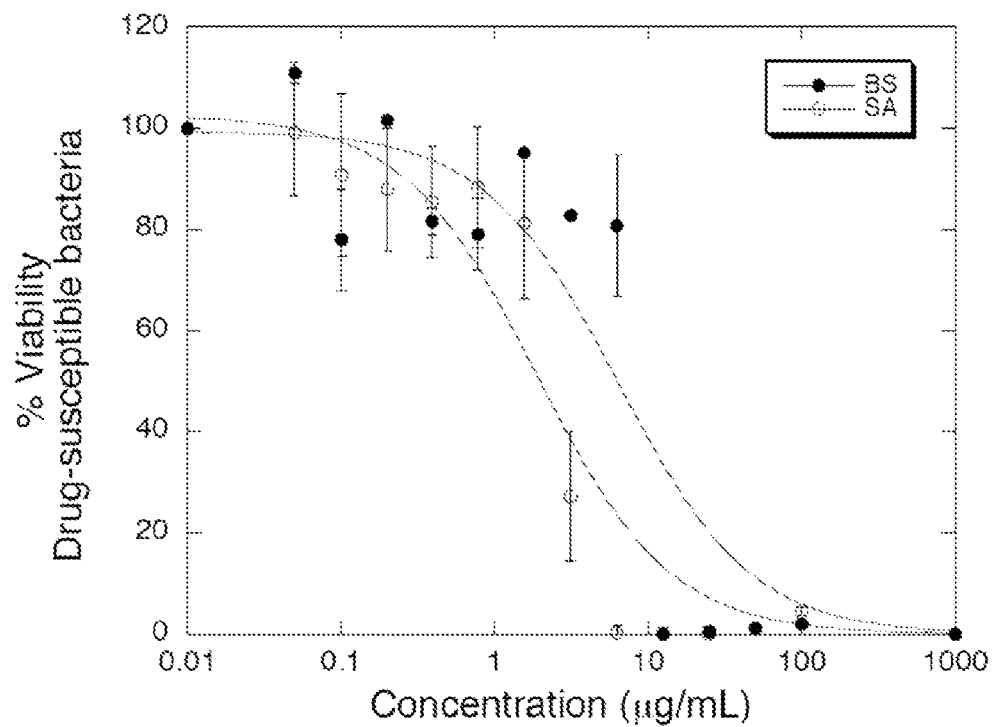
FIGS. 7A and 7B are dose-response curves for chrysophaentin 1 against various bacterial strains.
Figure 7B:
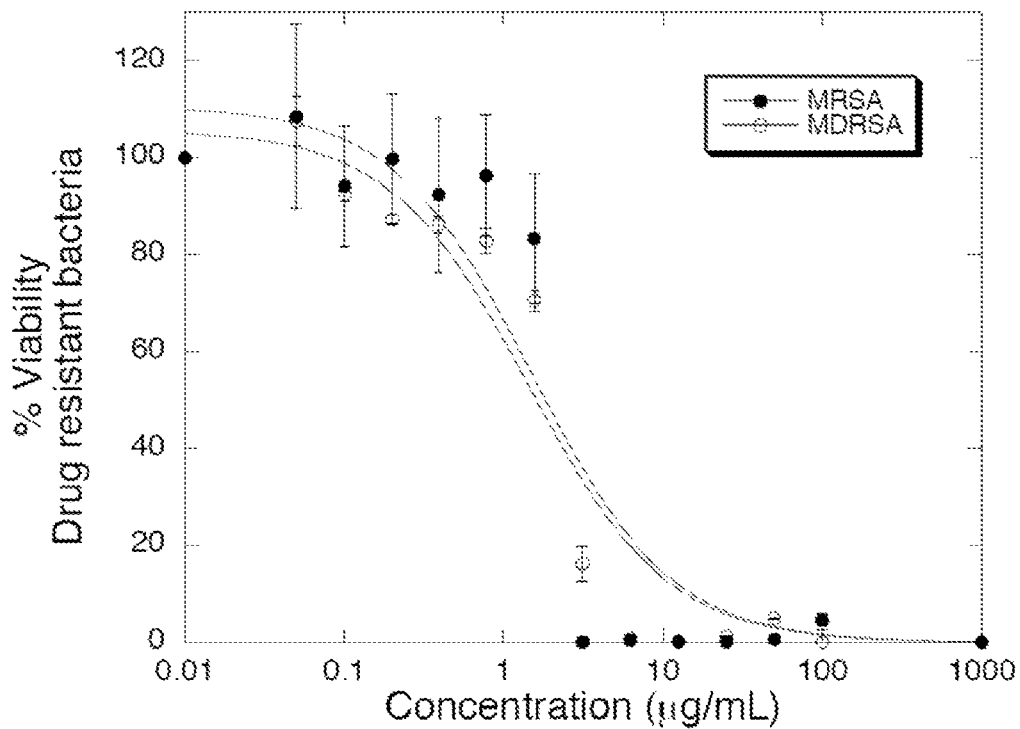
Figure 8:
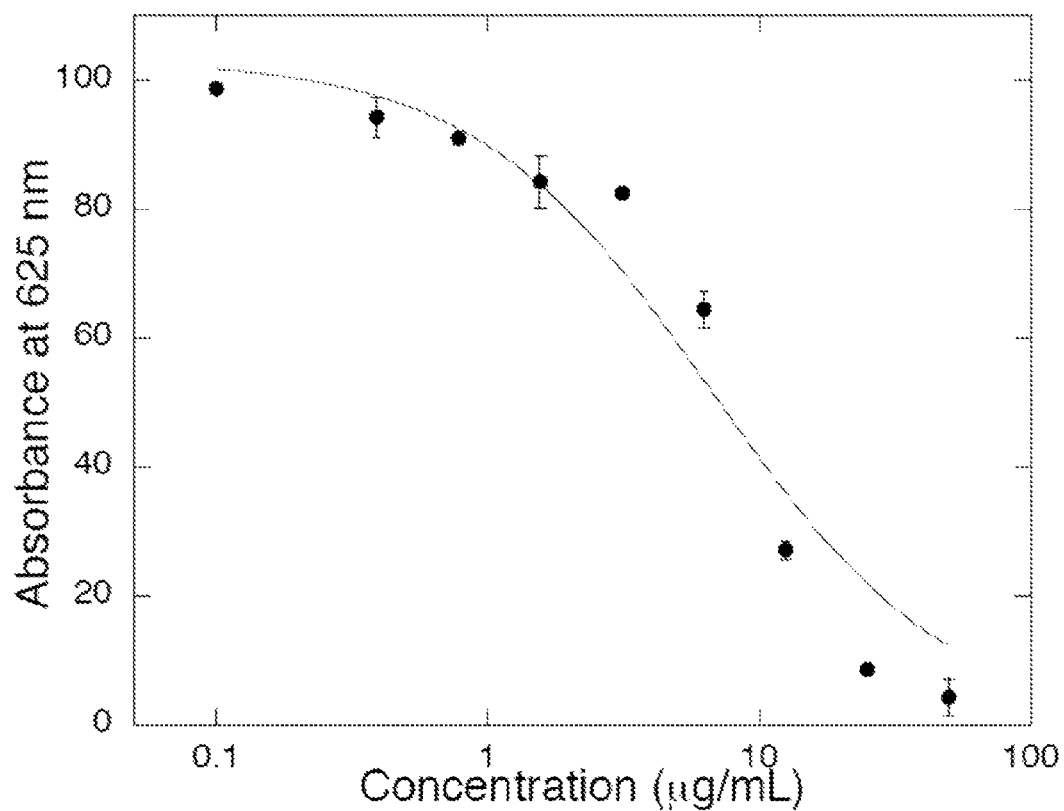
FIG. 8 is a graph of absorbance versus concentration demonstrating inhibition of FtsZ GTPase activity by chrysophaentin 1.

The results are shown in Table 7 and FIGS. 7A and 7B. FIG. 7A is a dose response curve for compound 1 in microbroth dilution assays against *S. aureus* (white circles) and *B. subtilis* (black circles). FIG. 7B is a dose response curve for compound 1 in microbroth dilution assays against MRSA (black circles) and MDRSA (white circles). Curves were fit to a one-site model with Kaleidagraph 4.0 using the equation y=100/[1+(concentration/$MIC_{50}$)], where $MIC_{50}$ is the concentration at which the growth of bacterial cultures are reduced by 50%. $MIC_{50}$ values were 1.8±0.6 μg/mL for SA, 1.5±0.7 μg/mL for MRSA, and 7.3±3.7 μg/mL for *B. subtilis*. Values for all compounds tested are shown in Table 7.

in FIG. 8, compound 1 was found to inhibit FtsZ with an $IC_{50}$ value of 6.7±1.7 μg/mL (9.9 μM).

Compound 1 was tested for its ability to inhibit FtsZ polymerization in vitro. Protofilament formation of *E. coli* FtsZ was assessed by polymerization assays. Solutions containing recombinant *E. coli* FtsZ (6 μM) in MES buffer were treated with 5% DMSO, or 50 μM compound 1 in 5% DMSO, for 2 minutes at room temperature, followed by addition of GTP. Following an additional 5 minutes incubation period at room temperature, aliquots (5 μL) were adsorbed onto carbon films on lacey carbon supports on 400-mesh copper grids, rinsed with $H_2O$, and exposed to 3% uranyl acetate for 5 minutes for negative staining. Images were acquired with an FEI Morgani transmission electron microscope, operating at 80 kV, and equipped with an AMT Advantage camera at 44,000× mag-

TABLE 7

Antimicrobial Data for Compounds 1, 1a, 4-8.

| Compound | Agar disk diffusion (μg/disk)[a] | | | | $MIC_{50}$ (μg/mL) | | | |
|---|---|---|---|---|---|---|---|---|
| | S. aureus | MRSA | E. faecium | VREF | S. aureus | MRSA | E. faecium | VREF |
| 1 | 2 | 2 | 2 | 2 | 1.8 ± 0.6 | 1.5 ± 0.7 | 3.5 + 1.8 | 2.8 ± 0.8 |
| 1a | NA[b] | NA | NA | NA | —[c] | — | — | — |
| 4 | 25 | 25 | 25 | 25 | >25 | 19.0 ± 5.9 | >50 | >25 |
| 5 | 25 | 10 | 25 | 25 | 10.5 ± 3.8 | 8.9 ± 2.8 | >25 | >25 |
| 6 | 10 | 10 | 10 | 10 | 5.3 ± 1.9 | 4.2 ± 1.2 | >25 | 9.5 ± 3.0 |
| 7 | NA | NA | NA | NA | 16.6 ± 5.3 | 12.3 ± 3.1 | >50 | 24.6 ± 7.3 |
| 8 | 5 | 5 | 10 | 10 | 4.5 ± 1.4 | 4.7 ± 1.4 | >25 | 9.4 ± 2.8 |

[a]Lowest concentrations leading to 8-10 mm zones of inhibition;
[b]NA, no zone of inhibition observed at 25 μg/disk;
[c]—, not tested.

In both assay formats, chrysophaentin 1 (compound 1) was the most potent antibiotic giving minimum inhibitory concentrations ($MIC_{50}$) of 1.8±0.6, 1.5±0.7, and 1.3±0.4 μg/mL against SA, MRSA, and multidrug-resistant SA (MDRSA), respectively; and 3.8±1.9 and 2.9±0.8 μg/mL toward *E. faecium* and VREF. Chrysophaentins 6 and 8 (compounds 6 and 8) were the next most potent compounds with $MIC_{50}$ values of 4-6 μg/mL toward *S. aureus* and MRSA, and ~9.5 μg/mL against VREF.

Example 3

GTPase Activity and FtsZ Polymerization

Figure 3:
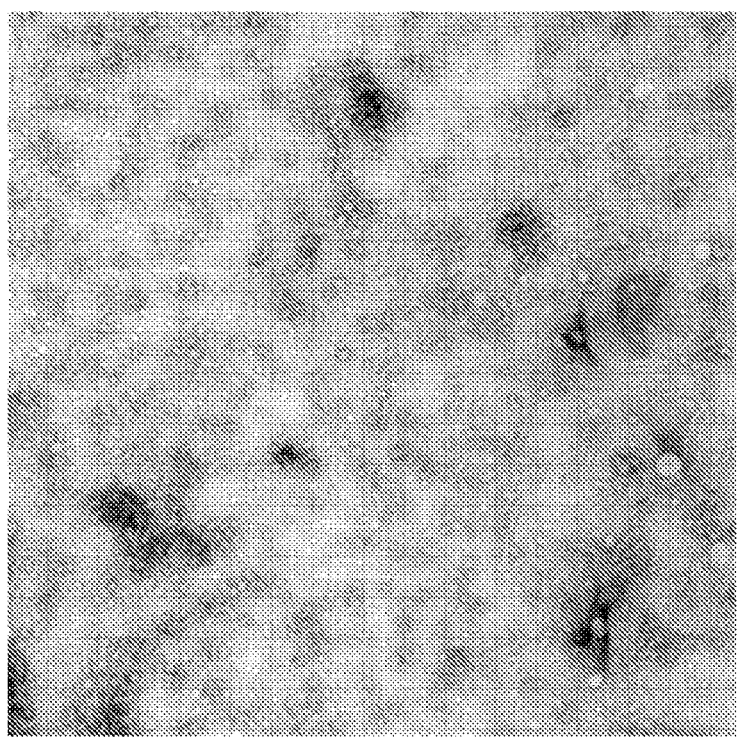
FIG. 3 is a transmission electron micrograph of FtsZ in the presence of GTP and chrysophaentin 1.

The bacterial cytoskeletal protein FtsZ is a GTPase and has structural homology to the eukaryotic cytoskeletal protein tubulin, but lacks significant sequence similarity. FtsZ is essential for bacterial cell division. Non-cleavable GTP-analogues have been reported to inhibit FtsZ in vitro, as have a handful of small molecules. Inhibition of FtsZ stops bacterial cell division and is a validated target for new antimicrobials. Compound 1 was tested for its ability to inhibit the GTPase activity of recombinant *E. coli* FtsZ using a colorimetric assay that detects release of inorganic phosphate ($P_i$) upon hydrolysis of GTP to GDP through complex with molybdate, also known as malachite green. GTPase assays were performed in 50 mM MES, pH 6.5, 50 mM KCl, 5 mM $MgCl_2$ in the presence of 2 μM FtsZ in the presence of varying concentrations of compound 1. Solutions were incubated at room temperature for 5 min, followed by addition of 0.25 mM GTP. At the end of a 20-min incubation period, enzyme activity was quenched by addition of 50 μL Malachite Green solution and the wells read at $A^{625}$ on an absorbance plate reader. As shown nification. As shown in FIG. 2, FtsZ polymerization was induced when GTP was added to recombinant *E. coli* FtsZ. In the presence of compound 1, however, polymerization and protofilament formation were inhibited, and no filaments were observed over the entire grid (FIG. 3).

Figure 9:
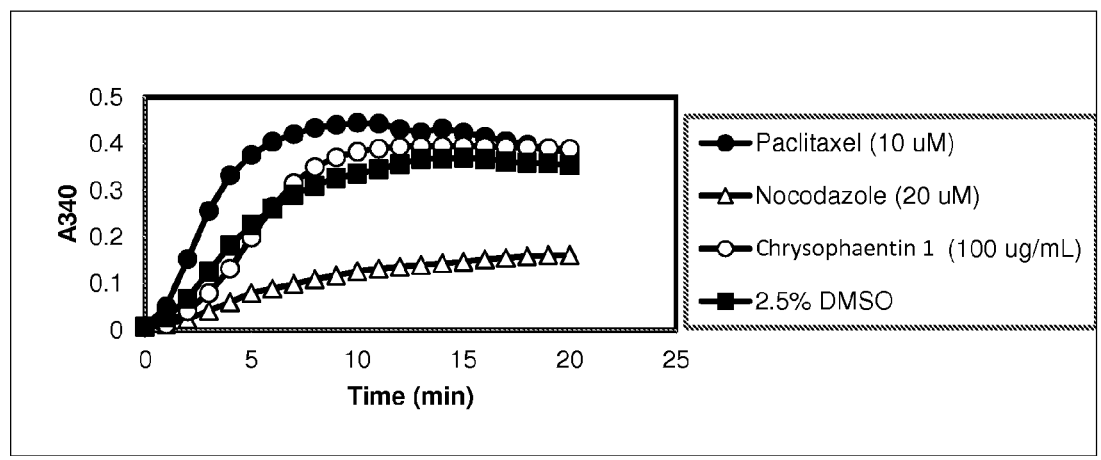
FIG. 9 is a graph of absorbance versus time demonstrating that chrysophaentin 1 does not affect tubulin polymerization.

Compound 1 also was tested for its ability to affect tubulin polymerization. Known microtubule stabilizing (paclitaxel) and disrupting (nocodazole) agents were tested at standardized concentrations, together with chrysophaentin 1 at 150 μM, a concentration 15 times greater than its $IC_{50}$ value for inhibition of FtsZ. DMSO (2.5%) was utilized as a control. As shown in FIG. 9, chrysophaentin 1 was found to have no effect on tubulin polymerization. Velocities are shown in Table 8.

TABLE 8

| Compound | v (min$^{-1}$) |
|---|---|
| paclitaxel | 80 |
| nocodazole | 12 |
| chrysophaentin 1 | 49 |
| DMSO (control) | 46 |

Example 4

Mode of Inhibition of FtsZ by Saturation Transfer Difference NMR

Saturation Transfer Difference (STD) NMR is an NMR technique that provides atomic level detail of the epitope used by a small molecule ligand to bind its macromolecular (protein) receptor. STD NMR was used to map the binding epitope of compound 1 in complex with recombinant FtsZ.

Figure 10:
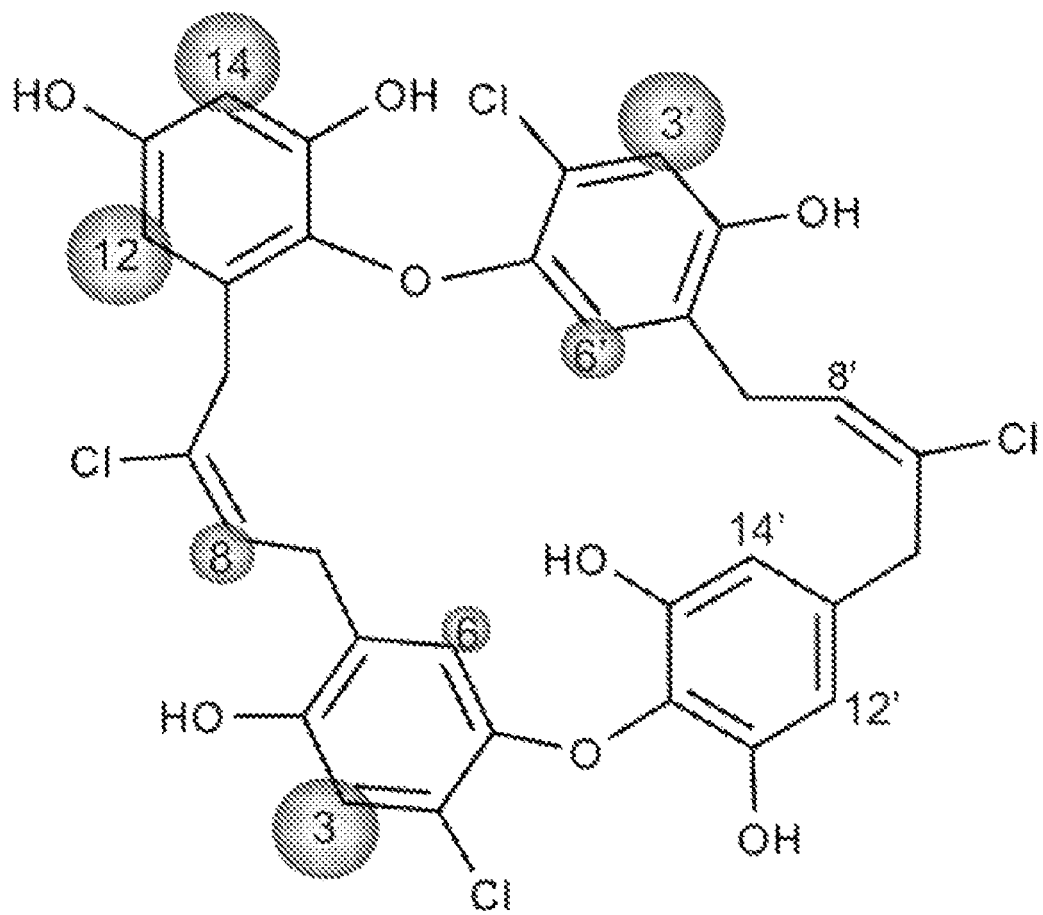
FIG. 10 depicts the percent enhancements observed in Saturation Transfer Difference NMR spectra recorded on samples containing chrysophaentin 1 in the presence of recombinant *E. coli* FtsZ.

Measurements were performed with NMR samples containing 10 μM FtsZ in the presence of 80-100-fold excess of compound 1, 20 mM NaPO$_4$, 50 mM NaCl, pH 6.8. Spectra of were recorded at 298 K with the carrier set at −1 or 12 ppm for on-resonance irradiation and 50 ppm for off-resonance irradiation. Selective protein saturation (duration ranging from 1 to 5 s) was accomplished using a train of 50 ms Gauss-shaped pulses, each separated by a 1 ms delay, at an experimentally determined optimal power (49 dB); a T1ρ filter (30 ms) was incorporated to suppress protein resonances. A minimum of 512 scans and 4000 points were used to ensure high quality data with good signal-to-noise. On- and off-resonance spectra were processed independently, and subtracted to provide a difference spectrum. Overlaid spectra were normalized to the signal for H-3 (δ 6.85), which gave the strongest enhancement (FIG. 4). STD enhancements were measured by integrating difference spectra where the peaks showing the strongest enhancements relative to the control spectra were used to normalize all non-overlapped peaks in the difference spectra. The STD enhancements for compound 1 binding to FtsZ are shown in FIG. 10. Shaded circles indicate protons in close proximity to FtsZ, where sizes of circles are proportional to percent enhancements.

In a separate experiment, guanosine 5'-(gamma-thio)triphosphate (GTPγS), a non-cleavable GTP analogue known by x-ray structures to bind in the GTP binding site of FtsZ, was titrated into the samples containing the complex of FtsZ and compound 1 and STD NMR experiments recorded as described above. The spectra are shown in FIG. 5 wherein spectrum A is an expanded $^1$H STD NMR spectrum of chrysophaentin 1 (1.25 mM) in the presence of FtsZ (12.5 μM) and no GTPγS, and spectra B-E were obtained from samples including 0.5, 1.0, 2.0, and 3.0 equivalents, respectively, of GTPγS. Upon addition of thio-GTP, enhancements corresponding to signals belonging to compound 1 diminished in intensity, while key signals assigned to thio-GTP increased in intensity. Thus, compound 1 is a competitive inhibitor of GTP binding to FtsZ, and binds in the GTP-binding site of FtsZ.

To support these experimental findings, molecular docking was performed using the coordinates of multiple bacterial FtsZ structures and compound 1. In all cases, the lowest energy docked pose corresponded to complexes where the inhibitor docked in the GTP-binding site of FtsZ (FIGS. 6A and 6B). Moreover, the orientation of binding in these models was consistent with the STD NMR experiments where protons exhibiting the largest enhancements were positioned most closely to the protein. This information reveals the mode of action and binding epitope of compound 1, both of which can be used for further medicinal chemistry optimization or in silico screening using the information provided from these experiments.

Example 5

Treatment with the Disclosed Compounds

A patient having a bacterial infection is selected for treatment. The patient may have a clinical presentation that suggests infection with an organism that would respond to the therapy. The clinical presentation may include, e.g., a fever, a cough, a urinary tract infection, gastrointestinal discomfort such as nausea, vomiting, and/or diarrhea, and/or evidence of a skin infection such as a festering, suppurating, or ulcerated wound, a boil, impetigo, or skin inflammation suggestive of cellulitis. Patients may be selected for treatment based on clinical judgment, or by performing in vitro assays of antimicrobial sensitivity before initiating treatment. For example, the patient may have apparent cellulitis suggestive of an infection *Staphylococcus aureus*. In other instances, a patient is selected based on culture-demonstrated susceptibility of an organism to a chrysophaentin compound or other laboratory testing (such as DNA analysis) that detects an organism for which treatment with a chrysophaentin may be beneficial, such as a *Staphylococcus aureus* or *Enterococcus faecium* infection. (See, e.g., Example 6.) In some instances, the patient may be infected with a drug-resistant bacterium such as methicillin-resistant *Staphylococcus aureus* (MRSA), multidrug-resistant *Staphylococcus aureus* (MDRSA) or vancomycin-resistant *Enterococcus faecium*. Alternatively, a patient may be selected after having failed treatment with methicillin, vancomycin or other antibiotics.

The patient is treated by administering a composition comprising at least one chrysophaentin at a dose determined by a clinician to be therapeutically effective. The chrysophaentin may be a compound according to any one of structures I-XI as described above, such as one or more of chrysophaentins 1-8. The composition also may include one or more second agents as described above. In some instances, the second agent is administered separately from the chrysophaentin and may even be administered by a different route. The patient may be treated by administering the composition intravenously, orally, topically, or rectally via a suppository. For severe infections, the route of administration will typically be intravenous administration, and the duration of treatment for a period of time sufficient to cure the infection or otherwise improve the clinical condition of the patient.

Example 6

Identification of a Subject in Need of Treatment with the Disclosed Compounds

A patient suspected of having a bacterial infection is selected for evaluation. The patient may be selected based on a clinical presentation (as described in Example 5) that suggests infection with an organism that would respond to the therapy. Prior to initiating treatment with a composition comprising at least one chrysophaentin, a specimen is obtained from the patient. Depending on the patient's clinical presentation and the clinician's assessment, the specimen may be a blood sample, a urine sample, a sputum sample, a stool sample, a wound culture, a throat swab, a nasal swab, or any other suitable specimen.

The specimen may be cultured in any suitable medium. For example, the specimen may be spread onto a plate of nutrient substance (e.g., agar) and allowed to grow for an effective period of time to produce a bacterial lawn. The bacterial species can be identified by examining/lawn characteristics (color, texture, growth pattern, etc.), Gram-staining, Ziehl-Neelsen staining, microscopic examination, metabolic/nutrient requirements, and even DNA sequencing. The bacterial sensitivity/susceptibility to various antibiotics also may be determined by placing small disks of filter paper and/or agar impregnated with various types of antibiotics, including chrysophaentin compounds, onto the bacterial lawn. The bacteria may then be incubated for an effective period of time (e.g., one to two days), and the plate may then be examined to see whether the bacterial growth is inhibited by one or more of the antibiotic disks. Sensitivity to an antibiotic may be determined by a clear "halo" or zone of inhibition around an antibiotic disk, indicating that the antibiotic has inhibited bacterial growth and/or killed the bacteria. A somewhat cloudy area around the disk may indicate some bacterial species in the sample are sensitive to the antibiotic while others are resistant to that antibiotic.

If the specimen includes bacteria that are known to be sensitive to a chrysophaentin and/or if bacterial species in the specimen show sensitivity to one or more chrysophaentins, the patient may be treated with a chrysophaentin as described above in Example 5. If the clinician has a strong suspicion that the patient may have a bacterial infection for which chrysophaentin treatment will be effective, the clinician may begin treating the patient with a composition comprising at least one chrysophaentin at a dose determined by the clinician to be therapeutically effective while awaiting results of the culture and sensitivity testing.

Embodiments of the disclosed compounds may have a structure according to formula I, II, or III as described herein. In some embodiments, the compound has formula I or formula II.

In any or all of the above embodiments, each $R^1$ may be independently hydroxyl or lower alkyl ester; each $R^2$, $R^3$ and $R^4$ may be independently halogen; and $R^5$ may be hydrogen or halogen. In any or all of the above embodiments, $R^1$ may be hydroxyl, each $R^2$ and $R^3$ independently may be chloro or bromo, $R^4$ may be chloro, and $R^5$ may be hydrogen or bromo.

In any or all of the above embodiments, the compound may have a formula according to any one of compounds 1-8 as described herein. In some embodiments, the compound has a formula according to compound 1, compound 4, compound 5, compound 6, compound 7, or compound 8.

In any or all of the above embodiments, the compound may have a $MIC_{50}$ in the range of 1 to 25 µg/mL against a bacterial pathogen which is being treated, or for which there is a clinical suspicion of its presence. In some embodiments, the target bacterial pathogen being treated is selected from *Staphylococcus aureus*, *Enterococcus faecium*, methicillin-resistant *Staphylococcus aureus* (MRSA), multidrug-resistant *Staphylococcus aureus* (MDRSA), vancomycin-resistant *Enterococcus faecium*, and combinations thereof. In some embodiments, the compound has a $MIC_{50}$ in the range of 1 to 5 µg/mL for methicillin-resistant *Staphylococcus aureus*, multidrug-resistant *Staphylococcus aureus* (MDRSA), or vancomycin-resistant *Enterococcus faecium*.

Embodiments of a pharmaceutical composition comprise a pharmaceutically acceptable carrier and a therapeutically effective amount of at least one compound according to formula I, II, or III as described herein, wherein the pharmaceutical composition is capable of inhibiting bacterial cell growth when applied to a bacterium. In some embodiments, $R^1$ is hydroxyl, $R^2$ and $R^3$ independently are chloro or bromo, $R^4$ is chloro, and $R^5$ is hydrogen or bromo.

In any or all of the above embodiments, the compound may be isolated from *Chrysophaeum taylori*. However, it need not be isolated from *C. taylori* or any other organism, but may instead be synthesized or otherwise obtained.

In any or all of the above embodiments, the pharmaceutical composition may further include a therapeutically effective amount of a second agent other than the compound. In some embodiments, the second agent is an antimicrobial agent. In some embodiments, the second agent is effective against Gram-negative bacterial cells. In certain embodiments, the second agent increases penetration of the compound into the bacterium.

Embodiments of a method for inhibiting bacterial cell growth include exposing a bacterium to an effective amount of a composition comprising a compound according to formula I, II, or III as described herein. In some embodiments, the compound is isolated from a marine organism. In particular embodiments, the marine organism is *Chrysophaeum taylori*. In any or all of the above embodiments, $R^1$ may be hydroxyl, each $R^2$ and $R^3$ independently may be chloro or bromo, $R^4$ may be chloro, and $R^5$ may be hydrogen or bromo.

In any or all of the above embodiments, the compound may have an in vitro $MIC_{50}$ in the range of 1 to 25 µg/mL against the bacterium. In any or all of the above embodiments, the bacterium may be a Gram-positive bacterium. In any or all of the above embodiments, the bacterium may be a drug-resistant bacterium. In some embodiments, the drug-resistant bacterium is methicillin-resistant *Staphylococcus aureus*, multidrug-resistant *Staphylococcus aureus*, or vancomycin-resistant *Enterococcus faecium*.

In any or all of the above embodiments, the composition may further include an effective amount of a second agent other than the compound. In some embodiments, the second agent is an antimicrobial agent. In certain embodiments, the antimicrobial agent is effective against Gram-negative bacterial cells. In some embodiments, the second agent increases penetration of the compound into the bacterium.

In any or all of the above embodiments, exposing the bacterium to an effective amount of the composition may include administering a therapeutically effective amount of the composition to a subject identified as being in need of antimicrobial treatment for a known or suspected bacterial infection. In some embodiments, the subject is identified as having a bacterium that is susceptible to treatment with the compound before administering the composition to the subject. In some embodiments, a second agent other than the compound is administered separately to the subject.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A compound according to formula I, II, or III

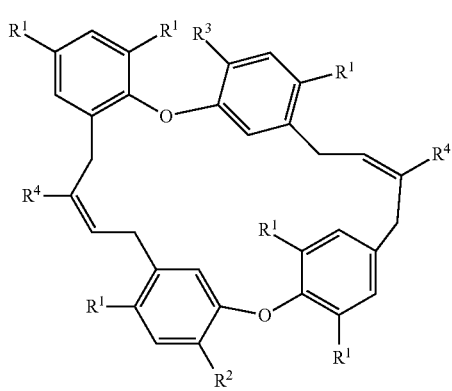

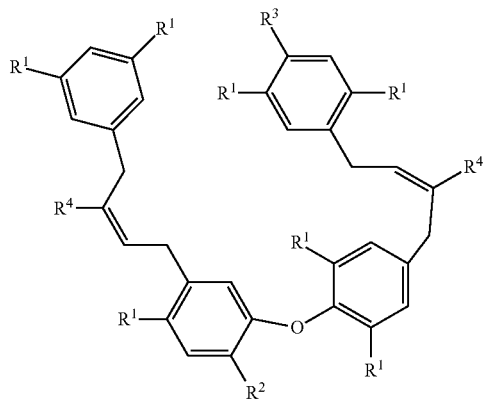

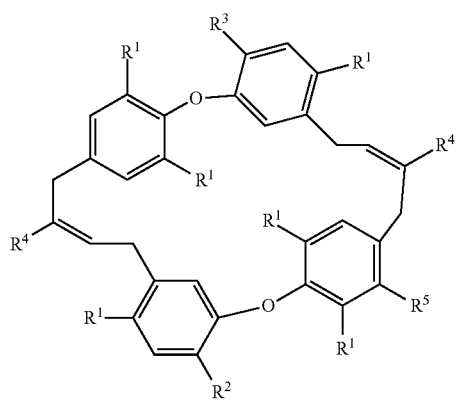

where each $R^1$ is independently hydrogen, hydroxyl, thiol, halogen, lower alkyl, lower alkoxy, or lower alkyl ester; and each $R^2$, $R^3$, $R^4$, and $R^5$ independently is hydrogen, hydroxyl, thiol, or halogen.

2. The compound of claim 1, wherein the compound has formula I or formula III.

3. The compound of claim 1, wherein:
each $R^1$ is independently hydroxyl or lower alkyl ester;
each $R^2$, $R^3$ and $R^4$ is independently halogen; and
$R^5$ is hydrogen or halogen.

4. The compound of claim 1, wherein:
$R^1$ is hydroxyl;
$R^2$ and $R^3$ independently are chloro or bromo;
$R^4$ is chloro; and
$R^5$ is hydrogen or bromo.

5. The compound of claim 1, having the formula

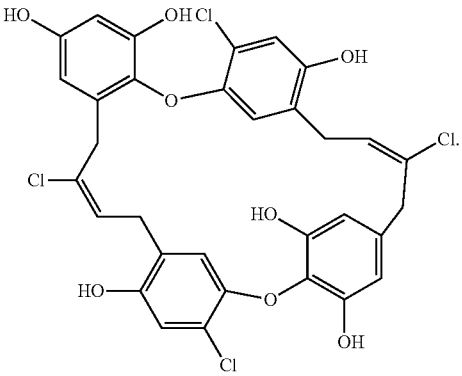 [SMILES: Oc1cc(O)c2c(c1)C/C(Cl)=C\Cc1cc(c(Cl)cc1O)Oc1c(O)cc(cc1O)C/C(Cl)=C\Cc1cc(c(Cl)cc1O)O2]

6. The compound of claim 1, having the formula

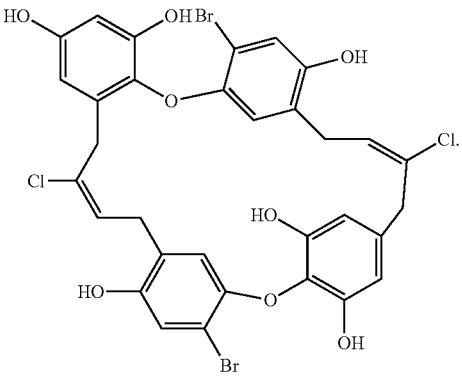 [SMILES: Oc1cc(O)c2c(c1)C/C(Cl)=C\Cc1cc(c(Br)cc1O)Oc1c(O)cc(cc1O)C/C(Cl)=C\Cc1cc(c(Br)cc1O)O2]

7. The compound of claim 1, having the formula

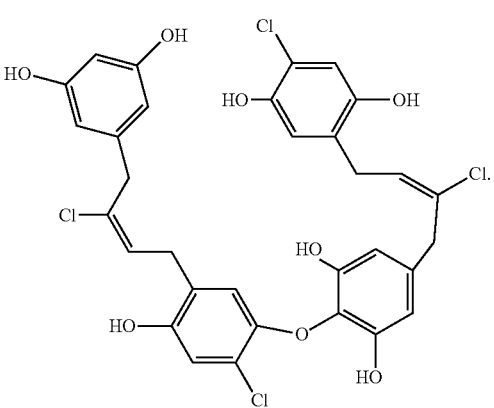 [SMILES: Oc1cc(O)cc(C/C(Cl)=C\Cc2cc(Oc3c(O)cc(C/C(Cl)=C\Cc4cc(O)c(Cl)cc4O)cc3O)c(Cl)cc2O)c1]

8. The compound of claim 1, having the formula

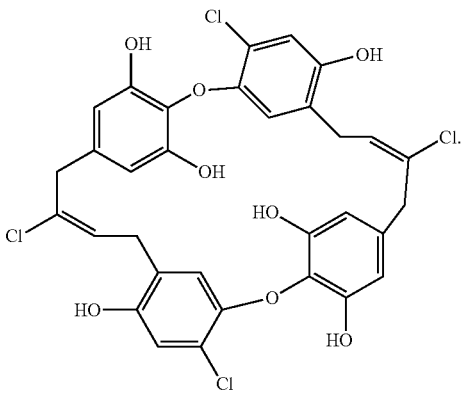 [SMILES: Oc1cc(Cl)c2cc1C/C=C(/Cl)Cc1cc(O)c(c(O)c1)Oc1cc(c(O)cc1Cl)C/C=C(/Cl)Cc1cc(O)c(c(O)c1)O2]

9. The compound of claim 1, having the formula

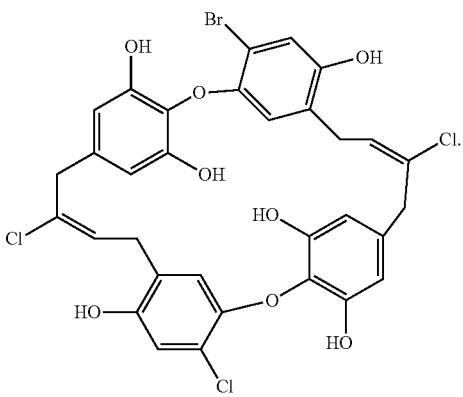 [SMILES: Oc1cc(Cl)c2cc1C/C=C(/Cl)Cc1cc(O)c(c(O)c1)Oc1cc(c(O)cc1Br)C/C=C(/Cl)Cc1cc(O)c(c(O)c1)O2]

10. The compound of claim 1, having the formula

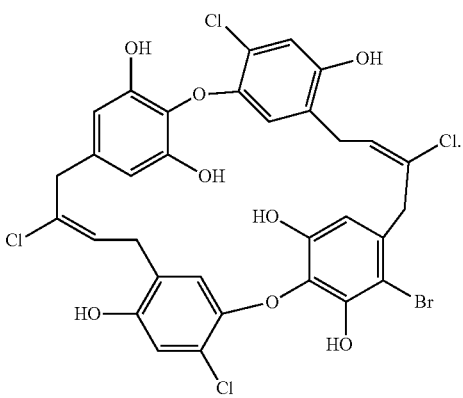 [SMILES: Oc1cc(Cl)c2cc1C/C=C(/Cl)Cc1cc(O)c(c(O)c1Br)Oc1cc(c(O)cc1Cl)C/C=C(/Cl)Cc1cc(O)c(c(O)c1)O2]

11. The compound of claim 1 having a $MIC_{50}$ in the range of 1 to 25 µg/mL when applied to at least one bacterial strain.

12. The compound of claim 11, wherein the bacterial strain is selected from *Staphylococcus aureus*, *Enterococcus faecium*, methicillin-resistant *Staphylococcus aureus* (MRSA), multidrug-resistant *Staphylococcus aureus* (MDRSA), vancomycin-resistant *Enterococcus faecium*, and combinations thereof.

13. The compound of claim 11, wherein the compound has a $MIC_{50}$ in the range of 1 to 5 µg/mL when applied to methi-cillin-resistant *Staphylococcus aureus*, multidrug-resistant *Staphylococcus aureus* (MDRSA), or vancomycin-resistant *Enterococcus faecium*.

14. A pharmaceutical composition, comprising a pharmaceutically acceptable carrier and a therapeutically effective amount of at least one compound according to claim 1 or a pharmaceutically acceptable salt, hydrate, or solvate thereof, wherein the pharmaceutical composition is capable of inhibiting bacterial cell growth when applied to a bacterium.

15. The pharmaceutical composition of claim 14, wherein:
$R^1$ is hydroxyl;
each $R^2$ and $R^3$ independently is chloro or bromo;
$R^4$ is chloro; and
$R^5$ is hydrogen or bromo.

16. The pharmaceutical composition of claim 14, wherein the compound is isolated from *Chrysophaeum taylori*.

17. The pharmaceutical composition of claim 14, further comprising a therapeutically effective amount of a second agent other than the compound.

18. The pharmaceutical composition of claim 17, wherein the second agent is an antimicrobial agent.

19. The pharmaceutical compound of claim 18, wherein the second agent is effective against Gram-negative bacterial cells.

20. The pharmaceutical composition of claim 17, wherein the second agent increases penetration of the compound into the bacterium.

21. A method of inhibiting bacterial cell growth, comprising exposing a bacterium to an effective amount of a composition comprising a compound according to claim 1 or a pharmaceutically acceptable salt, hydrate, or solvate thereof.

22. The method of claim 21, wherein the compound is isolated from a marine organism.

23. The method of claim 22, wherein the marine organism is *Chrysophaeum taylori*.

24. The method of claim 21, wherein:
$R^1$ is hydroxyl;
each $R^2$ and $R^3$ independently is chloro or bromo;
$R^4$ is chloro; and
$R^5$ is hydrogen or bromo.

25. The method of claim 21, wherein the compound has an in vitro $MIC_{50}$ in the range of 1 to 25 µg/mL against the bacterium.

26. The method of claim 21, wherein the bacterium is a Gram-positive bacterium.

27. The method of claim 21, wherein the bacterium is a drug-resistant bacterium.

28. The method of claim 27, wherein the drug-resistant bacterium is methicillin-resistant *Staphylococcus aureus*, multidrug-resistant *Staphylococcus aureus*, or vancomycin-resistant *Enterococcus faecium*.

29. The method of claim 21, further comprising exposing the bacterium to an effective amount of a second agent other than the compound.

30. The method of claim 29, wherein the second agent is included in the composition.

31. The method of claim 29, wherein the second agent is an antimicrobial agent.

32. The method of claim 31, wherein the antimicrobial agent is effective against Gram-negative bacterial cells.

33. The method of claim 29, wherein the second agent increases penetration of the compound into the bacterium.

34. The method of claim 21, wherein exposing the bacterium to an effective amount of the composition comprises administering a therapeutically effective amount of the composition to a subject identified as being in need of antimicrobial treatment for a known or suspected bacterial infection.

35. The method of claim 34, wherein the second agent is not included in the composition, and the second agent is administered separately to the subject.

36. The method of claim 34, further comprising identifying the subject as being infected with a bacterium that is susceptible to treatment with the compound before administering the composition to the subject.

* * * * *